(12) United States Patent
Porsgaard et al.

(10) Patent No.: US 11,604,159 B2
(45) Date of Patent: Mar. 14, 2023

(54) ELECTROCHEMICAL SENSOR WITH SMALL OPENING

(71) Applicant: SulfiLogger A/S, Risskov (DK)

(72) Inventors: Søren Porsgaard, Aarhus N (DK); Lars Hauer Larsen, Hinnerup (DK)

(73) Assignee: SulfiLogger A/S, Risskov (DK)

( * ) Notice: Subject to any disclaimer, the term of this patent is extended or adjusted under 35 U.S.C. 154(b) by 286 days.

(21) Appl. No.: 16/317,760

(22) PCT Filed: Jul. 14, 2017

(86) PCT No.: PCT/DK2017/050242
§ 371 (c)(1),
(2) Date: Jan. 14, 2019

(87) PCT Pub. No.: WO2018/010755
PCT Pub. Date: Jan. 18, 2018

(65) Prior Publication Data
US 2019/0219536 A1    Jul. 18, 2019

(30) Foreign Application Priority Data

Jul. 15, 2016 (EP) .................................... 16179812
Jul. 15, 2016 (EP) .................................... 16179814
Jul. 15, 2016 (EP) .................................... 16179815

(51) Int. Cl.
*G01N 27/404* (2006.01)
*G01N 27/40* (2006.01)
(Continued)

(52) U.S. Cl.
CPC ......... *G01N 27/4045* (2013.01); *G01N 27/40* (2013.01); *G01N 27/4072* (2013.01);
(Continued)

(58) Field of Classification Search
CPC .................... G01N 27/404; G01N 27/4045
See application file for complete search history.

(56) References Cited

U.S. PATENT DOCUMENTS

| 3,328,277 A | 6/1967 | Solomons et al. |
| 3,673,069 A * | 6/1972 | Niedrach ........... G01N 27/4162 204/414 |

(Continued)

FOREIGN PATENT DOCUMENTS

| DE | 41 31 927 A1 | 4/1993 |
| DE | 196 37 253 A1 | 3/1998 |

(Continued)

OTHER PUBLICATIONS

John Severinghaus, "A combined transcutaneous pO2-pCO2 electrode with electrochemical HCO3-Stabilization," The American Physiological Society, 1981, pp. 1027-1032 (Year: 1981).*

(Continued)

*Primary Examiner* — Alexander S Noguerola
(74) *Attorney, Agent, or Firm* — Knobbe Martens Olson & Bear LLP

(57) ABSTRACT

A electrochemical sensor (100) for sensing an analyte in an associated volume (106), the sensor comprising a first solid element (126), a second solid element (128) being joined to the first solid element, a chamber (110) being placed at least partially between the first solid element and the second solid element, a working electrode (104) in the chamber (110) and wherein one or more analyte permeable openings (122) connect the chamber with the associated volume (106) and wherein the electrochemical sensor (100) further comprises an analyte permeable membrane (124) in said one or more analyte permeable openings, and wherein the one or more analyte permeable openings are arranged so that a distance from any point in at least one cross-sectional plane to the (Continued)

nearest point of a wall of said opening is 25 micrometer or less.

37 Claims, 12 Drawing Sheets

(51) Int. Cl.
  *G01N 27/407* (2006.01)
  *G01N 33/00* (2006.01)
  *G01N 27/413* (2006.01)

(52) U.S. Cl.
  CPC ....... *G01N 27/413* (2013.01); *G01N 33/0044* (2013.01); *G01N 27/404* (2013.01)

(56) References Cited

U.S. PATENT DOCUMENTS

| | | | |
|---|---|---|---|
| 4,632,746 A * | 12/1986 | Bergman | G01N 27/404 204/415 |
| 4,711,703 A * | 12/1987 | Wright | G01N 27/404 165/177 |
| 4,842,713 A * | 6/1989 | Stahl | G01N 27/4077 204/424 |
| 4,851,088 A * | 7/1989 | Chandrasekhar | G01N 27/4045 205/782.5 |
| 4,859,292 A | 8/1989 | Appelby | |
| 5,004,532 A | 4/1991 | Hale | |
| 5,085,760 A | 2/1992 | Razaq et al. | |
| 5,102,525 A | 4/1992 | Miyahara et al. | |
| 5,690,808 A | 11/1997 | Akmal et al. | |
| 6,030,828 A | 2/2000 | Damgaard et al. | |
| 6,375,816 B1 | 4/2002 | Jach et al. | |
| 2006/0091010 A1 | 5/2006 | Komatsu et al. | |
| 2006/0237313 A1 | 10/2006 | Kiesele et al. | |
| 2008/0035493 A1 | 2/2008 | Sommer et al. | |
| 2010/0305420 A1 | 12/2010 | Curry | |
| 2014/0131224 A1 | 5/2014 | Kroener | |
| 2015/0369773 A1 | 12/2015 | Mett et al. | |

FOREIGN PATENT DOCUMENTS

| | | |
|---|---|---|
| DE | 10 2010 039 486 A1 | 2/2011 |
| EP | 2 075 576 A2 | 7/2009 |
| JP | 2006284400 | 10/2006 |
| WO | WO 2018/010753 A1 | 1/2018 |
| WO | WO 2018/010754 A2 | 1/2018 |

OTHER PUBLICATIONS

Hou et al., Hydrophobicity study or polytetrafluoroethylene nanocomposite films, Thin Solid Films 520 (2012) 4916-1920 (Year: 2012).*
Bochicchio et al., "Interaction of hydrophobic polymers with model lipid bilayers," Scientific Reports| 7:6357| published online Jul. 25, 2017 (Year: 2017).*
Online OxfordLearners Dictionaries definition of "entity" downloaded Apr. 7, 2021 from https://www.oxfordlearnersdictionaries.com/us/definition/english/entity (Year: 2021).*
Compound summary for "sulfide" on the PubChem website maintained by the NIH National Library of Medicine, downloaded on Amrch 23, 2022 from https://pubchem.ncbi.nlm.nih.gov/compound/sulfide (Year: 2022).*
Revsbech, Niels Peter "An oxygen microsensor with a guard cathode" Limnol. Oceanogr., 1989, pp. 474-478, vol. 34, No. 2.
Suzuki, Hiroaki et al., "Determination of blood $pO_2$ using a micromachined Clark-type oxygen electrode" Analytica Chimica Acta, 2001, pp. 249-259, vol. 431.
International Search Report for PCT/DK2017/050242 dated Nov. 7, 2017.
Spilker, et al., Journal of Electroanalytical Chemistry, 2008, 612, 121-130.

\* cited by examiner

ELECTROCHEMICAL SENSOR WITH SMALL OPENING

CROSS REFERENCE TO RELATED APPLICATIONS

This application is a U.S. National Phase Application of PCT International Application Number PCT/DK2017/050242, filed on Jul. 14, 2017, designating the United States of America and published in the English language, which is an International Application of and claims the benefit of priority to European Patent Application No. 16179815.2, filed on Jul. 15, 2016, European Patent Application No. 16179812.9, filed on Jul. 15, 2016, and European Patent Application No. 16179814.5, filed on Jul. 15, 2016. The disclosures of the above-referenced applications are hereby expressly incorporated by reference in their entireties.

FIELD OF THE INVENTION

The present invention relates to an electrochemical sensor, and more particularly to an electrochemical sensor with one or more small openings and a corresponding method and use.

BACKGROUND OF THE INVENTION

For numerous purposes, such as environmental monitoring, biological research, or wastewater treatment, it is beneficial to be able to sense or quantitatively measure the partial pressure or concentration of an analyte in an associated volume. This can be the partial pressure of a gas in a gas atmosphere or the concentration of a dissolved gas in a volume of liquid.

Electrochemical sensors for sensing an analyte in an associated volume have previously been proposed, but may be seen as being slow (such as slow during start-up and/or having long response times), fragile, bulky, flow dependent, unstable (such as having high baseline drift), difficult to manufacture and/or insensitive (with respect to the analyte).

An improved electrochemical sensor for sensing an analyte in an associated volume would be advantageous, and in particular a sensor presenting an improvement on one or more of the parameters mentioned above, would be advantageous.

SUMMARY OF THE INVENTION

It may be seen as an object of the present invention to provide an electrochemical sensor that solves the above mentioned problems of the prior art.

It is a further object of the present invention to provide an alternative to the prior art.

Thus, the above described object and several other objects are intended to be obtained in a first aspect of the invention by providing an electrochemical sensor (100) for sensing an analyte in an
- associated volume (106), the sensor comprising
- a first solid element,
- a second solid element being joined to the first solid element,
- a chamber (110), such as a chamber for comprising an electrolyte, such as a chamber for comprising an electrolyte solution, such as a chamber comprising an electrolyte, such as a chamber comprising an electrolyte solution, said chamber being placed at least partially between, such as fully between, the first solid element and the second solid element,
- a working electrode (104) in the chamber (110), such as in between the first solid element and the second solid element,
- a reference electrode (108), and
wherein one or more analyte permeable openings (122) connect the chamber with the associated volume (106), such as said one or more analyte permeable openings forming a diffusion barrier between the associated volume and the chamber, and wherein the electrochemical sensor (100) further comprises
- an analyte permeable membrane (124) in said one or more analyte permeable openings, such as a silicone membrane, such as a membrane which enables separating liquids (such as aqueous solutions) on either side of the one or more analyte permeable openings, and wherein the one or more analyte permeable openings, such as the one or more analyte permeable openings without the analyte permeable membrane, are arranged so that a distance from any point in at least one cross-sectional plane to the nearest point of a wall of said opening is 25 micrometer or less, such as 20 micrometer or less, such as 15 micrometer or less, such as 10 micrometer or less, such as 8 micrometer or less, such as 6 micrometer or less, such as 5 micrometer or less, such as 4 micrometer or less, such as 3 micrometer or less, such as 2 micrometer or less, where said cross-sectional plane is orthogonal to a direction of movement of an analyte diffusing from the associated volume to the working electrode along the shortest possible path.

The invention is particularly, but not exclusively, advantageous for obtaining an electrochemical sensor, which may be provided in a relatively simple manner, such as an automated manner and/or via microfabrication since the chamber is placed at least partially between, such as fully between, first and second solid elements. The sensor may furthermore be advantageous for having a relatively low stirring sensitivity, because the relatively small distance from any point in the opening to the wall of said opening may facilitate that depletion of analyte in front of the opening is minimized. The stirring sensitivity $S_{sen}$ is defined as:

$$s_{sen} = (c_{INF}/c_0) - 1,$$

where $c_{INF}$ is the concentration at infinite flow velocity in the associated volume and $c_0$ is the concentration measured without flow.

The above described object and several other objects are in particular intended to be obtained in a first aspect of the invention by providing the electrochemical sensor wherein the membrane (124) is not permeable to ions (which may alternatively be expressed as impermeable to ions. By 'not permeable to ions' may be understood substantially impermeable to ions, such as impermeable to ions. By 'substantially impermeable to ions' may be understood impermeable for ions in practical circumstances (such as in a context of an electrochemical sensor, such as a Clark-type sensor). By 'substantially impermeable to ions' may in particularly be understood as permeable or less permeable than any silicone or the silicone sealants obtainable from Dow Corning with product number 732 or 734. An advantage of having the membrane being impermeable to ions may be that it enables electrically isolating the chamber from the associated volume and/or that it facilitates maintaining an ionic composition of an electrolyte (such as an electrolyte solution) in the chamber.

A possible advantage of a small analyte permeable opening may be that it enables that a meniscus of a membrane material placed in fluid form in the opening has a smaller maximum distance from the point of the liquid surface closest to the associated volume to the point of the surface furthest away from the associated volume (as measured in a direction of movement of an analyte diffusing from the associated volume to the working electrode along the shortest possible path). This maximum distance may be described as the height of the meniscus from the bottom in the center to the top points at the side. This smaller maximum distance in turn renders the position of the end and/or beginning of the membrane material better defined, which in turn improves manufacturing tolerances, such as reducing inter-sensor variations.

A possible advantage of the sensor may be that a critical part of the sensor is robust, i.e. tolerant to mechanical shocks. Specifically, the sensor can pass the transit drop test method 516.6 (shock) described in standard MIL-STD-810G, which includes 26 drops from a height of 4 feet (1.22 meters) on a drop zone of two inches of plywood over concrete.

By 'the one or more analyte permeable openings are arranged so that a distance from any point in at least one cross-sectional plane to the nearest point of a wall of said opening is 25 micrometer or less, where said cross-sectional plane is orthogonal to a direction of diffusion movement of an analyte diffusing from the associated volume to the working electrode along the shortest possible path' may be understood that the shape and size of the one or more analyte permeable openings, such as the one or more analyte permeable openings without the analyte permeable membrane, are arranged so that an incompressible 50 micrometer diameter sphere would not be able to pass through the one or more analyte permeable openings. An advantage of this may be that it corresponds to a size wherein capillary forces may play a role, such as enable capillary filling, such as capillary filling controlled by the dimensions and/or materials, of the one or more analyte permeable openings.

By 'electrochemical sensor' is understood a sensor that detects the presence, such as measure the concentration, of an analyte (such as any one of nitrous oxide ($N_2O$), hydrogen sulfide ($H_2S$), oxygen ($O_2$), hydrogen ($H_2$), nitric oxide (NO)), by oxidizing or reducing the analyte (or a shuttle/mediator molecule) at the working electrode and detecting, such as measuring, the resulting current. It is understood that the resulting current need not necessarily be measured as a current, but may for example be measured as a voltage drop across a resistor. The words 'sensor' and 'electrochemical sensor' are generally used interchangeably within the context of the present application. In embodiments the electrochemical sensor comprises a voltage source, and a current meter.

By 'microfabricated' may be understood fabricated using one or more of four processes (comprising photolithography, thin-film growth/deposition, etching, and bonding) to create objects with one or more dimensions, such as at least one dimension decisive for performance, in the range of nanometer to micrometers, such as within 1 nanometer to 1 millimeter . In a microfabrication process, one may take a substrate and build a device out of its bulk material and/or on its surface. An example of a microfabricated sensor is given in the reference "*Determination of blood pO2 using a micromachined Clark-type oxygen electrode*" by Hiroaki Suzuki et al., Analytica Chimica Acta 431 (2001) 249-259, which reference is hereby incorporated by reference in entirety.

In an embodiment the sensor is a microsensor. By 'microsensor' may be understood a sensor with one or more dimensions, such as at least one dimension decisive for performance, in the range of micrometers, such as within 1 nanometer so 1000 micrometers, such as within 1 nanometer to within 500 micrometers, such as within 1 nm to within 300 micrometers, such as within 1 nanometer to 100 micrometers. The dimension in the range of micrometers may be referred to as a characteristic length. The dimension in the range of micrometers may be a diameter of an opening (or a maximum distance from a point in an inlet opening to the side of the inlet opening) or a distance from outside of the membrane (in the associated volume) through the membrane and to the working electrode.

By 'analyte' is understood the compound of interest, such as a molecule, such as $N_2O$, $H_2S$, $O_2$, $H_2$, or NO.

By 'sensing' is understood qualitatively detecting the presence of an analyte and/or quantitatively determining a partial pressure or concentration of analyte in the associated volume. In some more specific embodiments, sensing may be construed as quantitatively measuring a partial pressure of an analyte. It is understood that quantifying comprises qualifying.

By 'associated volume' is understood an associated volume which is adjacent the sensor and which may contain the analyte. The associated volume is not to be construed as limiting to the scope of the claims. The partial pressure of the analyte in the associated volume may be measured with the sensor. If the associated volume comprise a liquid, the concentration of analyte is related to the partial pressure via the solubility of the analyte. In order to avoid measuring the solubility, the sensor can be calibrated in solutions with known concentration. The associated volume may comprise a fluid, a gas or a matrix, such as any one of a biofilm, an extracellular matrix, a solid-liquid matrix (such as a sand-water matrix) and a solid-gas matrix (such as a sand-air matrix). The associated volume may be understood to start at the opposite side of the analyte permeable membrane with respect to the working electrode.

By 'chamber' is understood a chamber as is known in the art, such as a casing, which delimits a volume within the chamber from the surroundings external to the chamber. However, it is encompassed by the present invention, that the chamber may have one or more through-going holes in the delimiting walls, such as openings for filling or replacing electrolyte solution or openings for electrical wiring or membranes. However, in general, the chamber does not allow fluid passage, such as uncontrolled fluid passage, from outside the chamber to inside the chamber. The chamber may be suitable for comprising an electrolyte medium. 'Electrolyte medium' is an electrically conducting medium in which the flow of current is accompanied by the movement of matter in the form of ions, within which the analyte can diffuse. It is understood that the electrolyte medium electrically connects the reference electrode with ionic conductivity and the working electrode. The electrolyte medium may for example be an electrolyte solution (such as a liquid, such as a liquid which may ensure supply of ions to the working electrode where the analyte reacts for neutralizing reaction products), a gel electrolyte, a solid electrolyte or a paste electrolyte. By 'electrolyte solution' is understood a liquid comprising ions, wherein the charge carriers are dissolved ionic compounds. The chamber may encompass a part of the one or more analyte permeable openings, such as the part of the one or more analyte permeable openings on the chamber side of the analyte permeable membrane also being part of the chamber. Thus, the part of the analyte permeable openings which is on the chamber side of the analyte permeable membrane (such as on the opposite side of the analyte permeable membrane with respect to the associated volume) may be considered both part of the chamber and the one or more analyte permeable openings.

By 'first solid element' and 'second solid element' may be understood may be understood solid elements (which may each be a multilayer element) which may be joined at a common interface so as to encapsulate between them the chamber. The first and/or second solid element may be planar, such as the interface between them being planar. The first and/or second solid element may be formed in any one of silicon or glass. It is to be understood that the first and/or second solid element may comprise layers of materials, such as oxide or nitride layers, where the layers are then part of the first and/or second solid element. It is encompassed that the first solid element and/or the second solid element comprise a layer, such as a layer joined to another layer within the first or second solid element, that comprises the structure that forms the cavity for the chamber and the one or more openings once the first and second solid element are joined. The chamber and or the one or more membrane permeable openings may be at least partially formed as one or more non-through going holes in the first solid element and/or the second solid element.

By 'joined' may be understood that the first and second solid element are joined together, such as forming a fluid-tight bond at a common interface (where it is understood that the fluid-tight bond may comprise distinct openings, such as the one or more analyte permeable openings and/or one or more openings for electrolyte filling). Forming a fluid-tight bond may also be referred to as sealing the chamber by joining of the first and second solid element so as to form a sealing interface.

By 'said chamber being placed at least partially between the first solid element and the second solid element' may be understood that while at least some of the chamber may be placed between the first and second solid element, it is encompassed by the present invention, that the chamber may also comprise a volume extending beyond a volume between the first and second solid element. For example, in an embodiment, a casing is arranged for comprising a volume (an external reservoir, such a external to a volume between the first solid element and the second solid element) of the chamber which is outside a region between the first and second solid elements. An advantage of this may be that it enables forming delicate structures in small dimensions on small first and second solid elements, while still enabling having a large chamber volume, which may be arranged for holding a relatively large electrolyte volume (compared to a volume between the first and second solid elements), which may in turn enable extendeding a life time of the sensor.

By 'one or more analyte permeable openings' is understood one or more analyte permeable through-going holes in the structure around the chamber, which connect the associated volume with a volume within the chamber, such as directly connect the associated volume with the optional reaction region. By 'directly connect' may be understood that
   the optional reaction region is immediately adjacent to, such as abutting or overlapping, one side of the one or more analyte permeable openings and the associated volume may be immediately adjacent to the opposite side of the one or more analyte permeable openings, such that an analyte passing from the associated volume to the optional reaction region via the one or more analyte permeable openings need not pass the optional reservoir region,
and/or that
   the shortest distance from
      any point on the working electrode, through the one or more analyte permeable openings and the analyte permeable membrane to
      a point on the opposite side of the analyte permeable membrane with respect to the working electrode,
   is equal to or less than 300 micrometer.

It may be understood that the one or more analyte permeable openings form a diffusion barrier for analytes diffusing from the associated volume to the optional reaction region. The extent of an opening within the one or more analyte permeable openings may be understood to be a volume within the opening along a path through the respective opening, such as a path through the opening which is parallel with a direction of flow through the hole and which path intersects the middle (such as calculated analogously with a center of mass calculation) of the opening at the interfacial plane between the hole and the associated volume, from the associated volume to the working electrode, which volume is delimited on the associated volume side by
   a plane wherein the cross-sectional area of the opening first time (when moving from the associated volume to the working electrode) is less than 150% of the smallest cross-sectional area of the opening,
and delimited on the chamber side by
   a first plane (when moving from the the associated volume to the working electrode) comprising a part of the working electrode, and/or
   a plane wherein the cross-sectional area of the opening first time (when moving from the the associated volume to the working electrode) is more than 150% of the smallest cross-sectional area of the opening.

The cross-sectional area in this context is understood to be a cross-sectional area of said opening—without the analyte permeable membrane—in a plane orthogonal to said path.

The one or more analyte permeable openings have a membrane (where it is understood that the membrane may comprise a plurality of separate membranes, one in each analyte permeable opening in the case of a plurality of analyte permeable openings), but the membrane is analyte permeable. The one or more analyte permeable openings may be at an interface between the first and second solid element and/or as a one or more through-going holes in the first and/or second solid element.

By 'membrane' is understood a membrane material which is placed in the one or more analyte permeable openings (and optionally also in front of the one or more analyte permeable openings, such as a sheet in front of the one or more analyte permeable openings, said sheet optionally being a teflon™ sheet). More particularly, the membrane is at least placed in the one or more analyte permeable opening. The membrane is arranged so as to separate the associated volume from the volume within the chamber. More specifically, the membrane is situated so as to fill (and optionally also cover) the one or more analyte permeable openings, so as to block passage from the associated volume to the volume of any substance incapable of penetrating through the membrane. It is understood that the membrane may refer to a structure, such as a plug in an opening, that separates two fluids, such as a liquid or gas in the associated volume and a liquid in the chamber. It is understood, that the membrane may refer to a thin, film-like structure that separates two fluids, such as a liquid or gas in the associated volume, and a liquid or gas in the volume. However, it is also understood that the membrane may act as a selective barrier, allowing some species to pass through but not others. It is in particular understood, that the membrane is permeable to the analyte. It may furthermore be understood that the membrane is not permeable to ions. The membrane may in particular embodiment comprise, such as consist of, silicone, such as any one of the silicone sealants obtainable from Dow Corning with product number 732 or 734. The membrane may be understood to be impenetrable to the liquid electrolyte solution in the chamber (and the membrane may therefore enable retaining the liquid electrolyte solution in the chamber). It may be understood that while a molecule, e.g., $H_2O$ in liquid form cannot penetrate the membrane, the same molecule might be able to penetrate the membrane in gaseous form.

'Working electrode' is known in the art, and understood to be the electrode in the electrochemical sensor on which the reaction of interest is occurring. It may be understood that the reduction or oxidation of analyte (or a shuttle/mediator molecule) is taking place at the working electrode.

'Reference electrode' is known in the art, and understood to be the electrode in the electrochemical sensor, which has a stable well-defined electrochemical potential, and can receive or deliver electrons, from or to working and optional guard electrode reactions.

In an embodiment there is presented a sensor wherein said chamber (110) is comprising an electrolyte solution. In an embodiment there is presented a sensor wherein the electrolyte solution is a liquid comprising ions wherein charge carriers are dissolved ionic compounds.

In an embodiment there is presented a sensor wherein the membrane (124) enables separating liquids on either side of the one or more analyte permeable openings. This may allow for ensuring that the volume in the chamber is not contaminated with liquid from the associated volume and/or that the liquid in the chamber is not lost into the associated volume.

In an embodiment there is presented a sensor wherein the membrane (124) forms a hydrophobic barrier. This may allow for keeping aqueous liquids on either side of the membrane apart. More particularly, for example a gas that comes in contact with the sensor first passes through a (small capillary-type) opening and then diffuses through a hydrophobic barrier, and eventually reaches the electrode surface. This approach may be adopted to allow the proper amount of analyte to react at the sensing electrode to produce a sufficient electrical signal while preventing the electrolyte from leaking out of the sensor.

10 In an embodiment there is presented a sensor wherein the analyte permeable membrane (124) is a polymer, the analyte permeable membrane (124) is passive, and/or the analyte permeable membrane (124) is selective to non-ionic substances.

In an embodiment there is presented a sensor wherein one or more or all leads are at least partially placed on one or both of the first and second solid element at an interface where the first and second solid element are joined. This may allow for avoiding disadvantageous reactions at the leads.

In an embodiment there is presented a sensor wherein the sensor is a Clark-type sensor. By a 'Clark-type sensor' may be understood an electrochemical sensor where a (passive) membrane ensures a separation (such as electrical and ionic) between the associated volume and the working electrode (and more generally the sensor electrochemistry). Thus, the associated volume does not act as an electrolyte so the reference and the working electrode does not have electrical contact through a sample in the associated volume (such as blood). A Clark-type sensor is also known as an amperometric sensor, which is a sensor that produces an electrical current as a function of the analyte concentration (in the associated volume).

In an embodiment there is presented a sensor wherein
 a. the analyte permeable membrane is a polymer, such as an organic or inorganic polymer, such as silicone, such as fluorosilicone,
 b. the analyte permeable membrane is passive, such as not reacting with the diffusing species (such as the analyte), and
 c. the analyte permeable membrane is selective to non-ionic substances.

In another embodiment there is provided an electrochemical sensor, wherein the sensor further comprises a third electrode working as a counter electrode. 'Counter electrode' is known in the art and understood as an electrode which can deliver or receive electrons (i.e., current) from the working electrode. The counter electrode may also be referred to as an auxiliary electrode. An advantage using a counter electrode may be that less current runs between the working/guard electrodes and the reference electrode, which enhance the stability of the reference electrode.

'Reactants' are understood as is common in the art, such as a substance that is consumed in the course of a chemical reaction. More particularly, as reactants may be understood both (sought-after) analyte and unspecific species. In other words: By reactants from the optional reservoir region may be understood any species, which can lead to a reaction at the working electrode, which could give a signal, which could erroneously be interpreted as an analyte from the associated volume.

In an embodiment there is presented a sensor wherein said chamber comprising an electrolyte solution. The chamber may comprise (such as be filled with) at least 25 volume %, such as at least 50 volume %, such as at least 75 volume %, such as at least 90 volulme %, such as at least 95 volulme % electrolyte solution, such as 100 volume % electrolyte solution. There may be no gas phase between the working electrode and the analyte permeable membrane and/or there must be a continuous path of electrolyte solution between the working electrode and the analyte permeable membrane. The viscosity of the liquid electrolyte may be lower than 10,000 cP (Centipoise) (10 kilo cP).

In a further embodiment there is presented a sensor wherein the electrolyte solution being a liquid comprising ions wherein charge carriers are dissolved ionic compounds.

In an embodiment, there is provided a sensor wherein the analyte permeable membrane material could have been placed in the opening in the one or more analyte permeable openings by filling via a capillary force. By 'the analyte permeable membrane material could have been placed in the opening in the one or more analyte permeable openings by filling via a capillary force' may be understood that the analyte permeable membrane material could have been placed there in liquid form, and then (via the material properties of the liquid membrane material and the material properties of the surface of the walls of the opening and the dimensions of the opening) be dragged into the opening via capillary forces. An advantage of this may be, that the opening can in this way fill itself, e.g., if the membrane material is placed in liquid form next to and in contact with the opening.

In a furher embodiment, there is provided a sensor wherein said one or more analyte permeable openings and/or said chamber is further arranged so that the capillary force is so low at a position, such as at the end of the analyte permeable membrane material facing the chamber, that said capillary force could not drive said analyte permeable membrane material past said position. A possible advantage may be that the filling of the opening can be controlled by the material properties and dimenions of the opening, such as the length of the resulting membrane can be controlled very precisely because, e.g., the dimensions of the opening can be controlled very precisely (such as via microfabrication). Another possible advantage may be that it enables capillary filling without risking that the membrane material enters too deep into the chamber, such as ensuring that the membrane material does not reach the working electrode.

In a furher embodiment, there is provided a sensor wherein for at least one of the one or more analyte permeable openings the end of the analyte permeable membrane material (such as the analyte permeable membrane material of the at least one of the one or more analyte permeable openings) which faces the chamber is placed at (such as within a distance corresponding to 25% or less, such as 20% or less, such as 15% or less, such as 10% or less, such as 5% or less, such as 2% or less, such as 1% or less, of a length of the at least one of the analyte permeable membrane openings of)
d. the end of the at least one of the one or more analyte permeable openings which faces the chamber,
e. a position where at least one boundary surface of the at least one of the one or more analyte permable openings presents a kink, and/or
f. a position wherein an entity given as $(1/A)*dA/dz$ is equal to or larger than 1/micrometer, wherein A is area of a cross-section of the at least one of the one or more analyte permeable openenings, said cross-section being orthogonal to a path through the opening, and z is a position along the path through the at least one of the one or more analyte permeable openings.

An advantage of this may be, that the analyte permeable membrane stops at a geometrically well-defined position, such as a position which may be well-defined during (micro-)fabrication of the sensor (and more particularly the fabrication of the opening and/or the chamber). By a 'kink' may be understood a position where one of the walls of an opening changes direction by more than 5 degrees, such as more than 25 degree, such as more than 45 degrees, such as more than 90 degrees, within 5 micrometers.

In an embodiment there is presented a sensor wherein one or more or all boundary walls of the one or more analyte permeable openings have a non-rectilinear shape, such as a curved or piecewise rectilinear shape, such as a zig-zag shape, such as wherein the one or more analyte permeable openings have different cross-sectional areas at different positions. A possible advantage of this may be that a membrane placed in the one or more analyte permeable openings may be more robustly placed there (e.g., with respect to a differential pressure on either side of the opening), for example if displacement of the membrane entails deformation of the membrane, such as wherein the membrane has different widths at different positions so that a displacement of the membrane would entail squeezing a relatively wide section of the membrane through a section of the hole which is relatively narrow.

In an embodiment, there is presented a sensor which endures a differential pressure of 4 bar or more, such as 5 bar or more, such as 10 bar or more, such as 25 bar or more, such as 50 bar or more, such as 100 bar or more. In general, an advantage of the present sensor may be, that it may be constructed so as to endure exposure to high pressure (relative to atmospheric pressure). For example, the sensor may endure a differential pressure (on either side of the analyte permeable membrane, such as the difference in pressure one one side of the membrane with respect to the pressure on the other side, such as the difference in pressure in the associated volume with respect to the chamber) of at least 4 bar. The present inventors have made the insight that the ability of the sensor to endure high pressure may be achived in a plurality of different ways, including having areas of the one or more analyte permeable openings being small and/or by having the membrane being relatively long (such as relative to said areas) and/or wherein one or more or all boundary walls of the one or more analyte permeable openings have a non-rectilinear shape.

In an embodiment there is presented a sensor wherein an angle between a boundary wall of the one or more analyte permeable openings at the end of the one or more analyte permeable openings which faces the chamber and an abutting wall of the chamber is more than 270 degrees, such as more than 271 degrees, such as more than 275 degrees, such as more than 280 degrees, such as more than 290 degrees, such as more than 300 degrees, such as more than 315 degrees, such as more than 330 degrees, such as 345 degrees or more. A possible advantage of this may be that it enables increasing the capillary forces at the end of the one or more analyte permeable openings.

In an embodiment there is presented a sensor wherein an angle between a boundary wall of the one or more analyte permeable openings at the end of the one or more analyte permeable openings which faces the chamber and an abutting wall of the chamber is more than 285 degrees.

In an embodiment there is presented a sensor wherein
g. the analyte permeable membrane is a polymer, such as an organic or inorganic polymer, such as silicone,
h. the analyte permeable membrane is passive, such as not reacting with the diffusing species, and
i. the analyte permeable membrane is selective to non-ionic substances.

In an embodiment, there is presented a sensor wherein the chamber comprises:
a reaction region (130), and
a reservoir region (132) being connected with the reaction region,
and wherein the electrochemical sensor (100) further comprises
a guard electrode (109) arranged so as to enable reduction or oxidation of at least some reactants from at least a part of the reservoir region, such as reactants which could otherwise diffuse to the working electrode (104) and be reduced or oxidized at the working electrode, wherein the guard electrode comprises a thin film, such as a thin film placed on an inner wall of the chamber.

A possible advantage of this may be that the sensor may furthermore be robust due to the incorporation of the guard electrode as a thin film electrode since the thin film enables efficiently fixing the guard to an inner wall of the chamber. The sensor may furthermore be seen as enabling a high level of stability over extended periods of time since the incorporation of the guard as a thin film enables both long-time operation due to efficient exchange of electrolyte species, such as ions, at the working electrode (in the reaction region) and low drift by having reactants from the reservoir effectively reduced or oxidized when they pass the guard electrode. Furthermore, the guard electrode may ensure fast start-up, since it enables cleaning up the reservoir region of the chamber, so that a false-positive signal from reactants diffusing from the reservoir region is effectively reduced or eliminated.

By 'reaction region' is understood a region of the chamber which is closer to the working electrode than the guard electrode.

By 'reservoir region' is understood any portion of the chamber outside of the reaction region, such as defined as the part of the chamber, which is closer to the guard electrode than the working electrode.

The feature 'the reservoir region being connected, such as fluidically connected, with the reaction region' may be understood to specify, that ions, such as counter ions in the electrolyte, may diffuse from the reservoir region to the reaction region. This may be enabled by having the reservoir region and the reaction region being fluidically connected and/or connected by an electrolyte medium, such as an electrolyte solution or a gel electrolyte or a paste electrolyte or a solid electrolyte.

By 'guard electrode' is understood an additional electrode with respect to the working electrode, such as an additional cathode or anode, which is arranged so as to enable reduction or oxidation of at least some reactants from at least a part of the reservoir region, such as reactants which could otherwise diffuse to the working electrode and be reduced or oxidized at the working electrode. The guard electrode may alternatively be referred to as "scavenging electrode" or "protecting electrode". By 'arranged so as to enable reduction or oxidation of at least some reactants from at least a part of the reservoir region' may be understood that the guard electrode has a size large enough and a position sufficiently close to possible paths from the reservoir region to the reaction region, so that it may reduce or oxidize the reactants. An advantage of this may be that said reactants cannot then cause a false positive signal or noise at the working electrode. A guard electrode is described in "*An oxygen microsensor with a guard cathode*", NP Revsbech, Limnol. Oceanogr., 34(2), 1989, 474-478, which is hereby incorporated by reference in entirety.

The guard electrode may be implemented as a thin film at an inner wall of the chamber, such as on the first and/or second solid element. An advantage of this may be that the first/and or solid element then double functions as chamber wall and supporting structure for the guard. Another advantage may be, that the guard can be implemented in a way wherein it occupies substantially zero volume in the chamber and causes not obstruction to diffusion within the chamber. Another possible advantage may be that the position of the guard with respect to the chamber is fixed, such as fixed in a robust way.

By 'thin film' is understood a layer of material having a thickness within a thickness corresponding to an atomic monolayer of the material to one or more micrometers, such as to 1 micrometer, such as to 2 micrometer, such as to 5 micrometer, such as to 10 micrometer, in thickness, where 'thickness' may be understood as a length through the material along its smallest dimension, which may generally be a dimension which is parallel with a surface normal of a surface upon which the thin film is placed. It may also be understood that a thin film is a structure, where at least a part of it has a primary size (such as width and/or length) in a first and/or second direction, which first and second directions are orthogonal to each other, while a secondary size (such as a length, such as a height or thickness) in a third direction, which is orthogonal to the first direction and the second direction, is smaller than the primary size, such as a ratio between the primary size, and
the secondary size, is at least 10:1, such as at least 100:1, such as at least 1000:1.

The thin film may be placed at the electrochemical sensor by deposition or growth on a solid surface of the sensor, such as the first or second solid element. By 'deposition' or 'growth' is understood any process of placing a material on a surface in an additive manner, such as physical deposition (e.g., physical vapour deposition (PVD), molecular beam epitaxy (MBE), electron beam evaporation, sputtering, pulsed laser deposition (PLD), ion beam deposition, cathodic arc deposition (arc-PVD), electro hydrodynamic deposition) or chemical deposition (chemical vapour deposition (CVD), plating, spin coating, atomic layer deposition (ALD), chemical beam epitaxy). The thin film can also be deposited on the whole solid surface and thereafter removed, such as etched away, in selected areas.

In an embodiment, there is presented a sensor wherein the one or more analyte permeable openings are placed at least partially, such as fully, between the first solid element and the second solid element.

A possible advantage of this may be that it allows freedom in design of the one or more analyte permeable openings in a relatively simple manner, because they can for formed as a cavity in the first and or second solid element before joining of the first and second solid elements. This may enable design and manufacture, such as relatively simple manufacture, of openings with relatively complicated geometries (sizes and or shapes), such as elongated (high aspect ratio), curved, zig-zag shaped walls.

By 'the one or more analyte permeable openings are placed at least partially between the first solid element and the second solid element' may be understood that an opening borders on both the first solid element and the second solid element (such as is abutting, such as touching, both the first solid element and the second solid element), such as being enclosed only partially by each of the first solid element and the second solid element. An interface between the first solid element and the second solid element, such as a bonding interface, may define an interface plane, and it may be understood that an analyte may travel from the associated volume to the chamber, such as to the working electrode, via a path confined in a plane being parallel with, such as identical to, said interface plane. A distance from the first solid element to the second solid element in a direction orthogonal to the interface plane and in the chamber between the first solid element and the second solid element (such as a maximum distance at the position of the working electrode) is 50 micrometers or less, such as 25 micrometers or less, such as 10 micrometers or less, such as 5 micrometers or less. A possible advantage of this may be that it facilitates a small chamber volume and ensures that any analyte comes close to the working electrode.

In an embodiment, there is presented a sensor wherein the sensor comprises a plurality of analyte permeable openings. The openings can be placed in a row and/or in a grid. Alternatively, the openings can be placed at arbitrary positions. An advantage of having a plurality of analyte permeable openings may be, that it increases the area of the opening (which may be beneficial for having a large amount of analyte reaching the working electrode, which in turn may yield a larger signal and enhance sensitivity), without increasing the size of the individual holes (where a relatively smaller size each individual opening may be beneficial for reducing a flow dependence). Thus, having a plurality of openings may be beneficial for overcoming the otherwise necessary tradeoff between high sensitivity and stirring sensitivity. Another possible advantage may be that for a given total area the individual openings may have smaller widths (or diameters in case of circular cross-sections), which may in turn enable that a meniscus of a membrane material placed in fluid form in the openings has a smaller radius of curvature. Another possible advantage may be that for a given total area the individual openings may have smaller widths (or diameters in case of circular cross-sections), which may in turn enable that a meniscus of a membrane material placed in fluid form in the openings has a smaller maximum distance from the point of the liquid surface closest to the associated volume to the point of the surface furthest away from the associated volume (as measured in a direction of movement of an analyte diffusing from the associated volume to the working electrode along the shortest possible path). This maximum distance may be described as the height of the meniscus from the bottom in the center to the top points at the side.

In an embodiment, there is presented a sensor wherein the first solid element is joined to the second solid element by bonding, such as permanent bonding, such as anodic bonding and/or wherein the first solid element and/or the second solid element comprises at least 20 wt % silicon, such as at least 50 wt % silicon, such as at least 75 wt % silicon, such as at least 99 wt % silicon, such as 100 wt % silicon. By 'bonding' is understood a method of joining, such as permanently and/or irreversibly joining, two surfaces by chemical and/or physical forces, such as chemical and/or physical bonds. Bonding, such as permanent bonding, can be achieved using any one of anodic bonding, fusion bonding, direct bonding, eutectic bonding and adhesive bonding. An advantage of bonding the first and second solid element together may be that it enables forming in a relatively simple, efficient and compact manner a fluid tight interface between the first and second solid element. Another possible advantage of bonding, such as anodic bonding, may be that it enables electrically isolating the electrical connections (leads) to the electrodes by having the leads placed between the first and second solid element. It may be understood that one or more or all the leads (which may be thin films) may be placed on one or both of the first and second solid element, such as wherein joining (such as bonding) the first and second solid elements may simultaneously embed and encapsulate the leads in the resulting sandwich structure. An advantage of anodic bonding may be, that it enables having leads on the first and or second solid element, such as on surface of the first and/or second solid elements which are bonded to the opposite element, where said leads may be of non-zero height above the surface, such as for example 100 nm.

An advantage of having the first and/or second solid element comprising silicon may be that it facilitates that the sensor can be produced via readily available microfabrication processes, which are applicable for silicon-based materials.

In an embodiment, there is presented a sensor wherein a plane may be defined which is parallel with and tangential with a boundary wall of each of, such as each and all of:
The chamber, such as the reaction region and the reservoir region, and
At least one of the one or more analyte permeable openings.

For example, a plane may be parallel and tangential with a surface of the first solid element, which is itself planar and serves as a lid on top of the second solid element wherein a cavity is formed which correspond to at least part of the chamber (such as with the reaction region and at least part of the reservoir region) and at least one of the one or more analyte permeable openings. An advantage of this may be that the planar (first) solid element can be kept very simple and/or that the requirements to alignment of the first solid element can be kept relatively relaxed. In another example, which may be combined with the previous example, a cavity is formed in the first and or second solid element, which cavity correspond to the chamber (such as with the reaction region and at least part of the reservoir region) and at least one of the one or more analyte permeable openings, and where a plane may be parallel and tangential with a bottom boundary surface of both the chamber (such as with the reaction region and at least part of the reservoir region) and at least one of the one or more analyte permeable openings. An advantage of this may be that it enables forming said cavity in quite simple way, e.g., by etching to the same depth everywhere, and or placing, such as depositing, boundary surfaces of the same height everywhere. By 'bottom' is in this context understood the boundary wall in an element, which is parallel with and opposite a boundary wall on the opposite solid element.

In an embodiment, there is presented a sensor wherein one or both of:
The working electrode (104), and
The reference electrode (108),
comprise a thin film. An advantage of this may be that all electrodes may be provided simultaneously, such as in the same process step, e.g., deposited through a mask. Another possible advantage may be, that it enables providing multiple electrodes of the same kind, such as multiple working electrodes. It may be understood that in case a plurality of electrodes are implemented as thin film electrodes they may all be on the first solid element or on the second solid element or there may be at least one electrode on the first solid element and at least one other electrode on the second solid element.

In an embodiment, there is presented a sensor wherein a distance between
the working electrode
and
a point in the reaction region which is furthest away with respect to the working electrode
is 500 micrometer or less, such as 250 micrometer or less, such as 100 micrometer or less, such as 50 micrometer or less, such as 25 micrometer or less, such as 10 micrometer or less, such as 5 micrometer or less. An advantage of this may be that having a relatively small distance between the working electrode and the point in the reaction region which is furthest away with respect to the working electrode (where said distance is understood to be measured as the distance a substance, such as a reactant, would have to travel, such as diffuse, from said point to the working electrode), entails that a period of time from starting the sensor until a steady baseline signal is achieved is relatively small, because said period of time depends on the actual time it takes from a substance to travel said distance.

In an embodiment, there is presented a sensor wherein a distance between
the working electrode
and
a point in the reaction region which is furthest away with respect to the working electrode
is 50 micrometer or less, such as 25 micrometer or less, such as 10 micrometer or less, such as 5 micrometer or less.

In an embodiment, there is presented a sensor wherein an area, such as an area in the chamber or at a wall of the chamber, covered by the working electrode is equal to or less than 2500 square micrometer, such as equal to or less than 2000 square micrometer, such as equal to or less than 1500 square micrometer, such as equal to or less than 1000 square micrometer, such as equal to or less than 600 square micrometer, such as equal to or less than 250 square micrometer, such as equal to or less than 100 square micrometer, such as equal to or less than 75 square micrometer, such as equal to or less than 50 square micrometer, such as equal to or less than 25 square micrometer, such as equal to or less than 10 square micrometer. A possible advantage of this may be that the zero current from unspecific reactions on the working electrode is minimized while maintaining the sensitivity. The small size may also make it possible to place the guard electrode very close to the analyte permeable opening and thereby minimize the volume of the reaction region.

In an embodiment, there is presented a sensor wherein a smallest (such as at the position where the opening is narrowest) total cross-sectional area of the one or more analyte permeable openings (122) in a cross-sectional plane being orthogonal to a direction of movement of an analyte diffusing from the associated volume to the working electrode along the shortest possible path is equal to or less than 0.25 square millimeter, such as equal to or less than 0.10 square millimeter, such as equal to or less than 0.05 square millimeter, such as equal to or less than 0.01 square millimeter, such as equal to or less than 0.005 square millimeter, such as equal to or less than 0.0025 square millimeter, such as equal to or less than 2500 square micrometer, such as equal to or less than 1000 square micrometer. A possible advantage of having a relatively small smallest total cross-sectional area of the one or more analyte permeable openings (122) may be that the smallness of this area facilitates little evaporation from the chamber and little influx of, e.g., contaminants or water vapour into the chamber. Another possible advantage may be that it facilitates drawing only a low current, e.g., less than 1 nA at the working electrode, which may in turn facilitate extended lifetime and/or low stirring sensitivity.

In an embodiment, there is presented a sensor wherein a ratio ($A_{min,opening}/A_{min, WE-Ref}$) between
  A first smallest total cross-sectional area ($A_{min,opening}$) of the one or more analyte permeable openings (122) in a cross-sectional plane being orthogonal to a direction of movement of an analyte diffusing from the associated volume to the working electrode along the shortest possible path, and
  A second smallest total cross-sectional area ($A_{min, WE-Ref}$) of the chamber along a shortest possible path of a species diffusing from the working electrode (WE) to the reference electrode (Ref), said second smallest cross-sectional area ($A_{min, WE-Ref}$) being in a cross-sectional plane being orthogonal to a direction of movement of a species diffusing from the working electrode (WE) to the reference electrode (Ref) along the shortest possible path,
is equal to or less than 1, such as equal to or less, such as equal to or less than 0.5, such as equal to or less than 0.1, such equal to or less than 0.05, such as equal to or less than 0.01, such as equal to or less than 0.001. An advantage of this embodiment may be that it ensures that for an opening area ($A_{min,opening}$)—which allows an amount of analyte to enter the chamber an be reduced or oxidized at the working electrode and thereby generate reaction products—at least the same area is available for species diffusing to and from the reference (from to the working electrode). An possible advantage of this may be, that it may ensure or facilitate that there will be little or no buildup of reaction products at the working electrode.

In an embodiment, there is presented a sensor wherein the first solid element comprises, such as consists of, silicon and/or wherein the second solid element comprises, such as consists of, borosilicate.

In an embodiment, there is presented a sensor wherein the first solid element and the second solid element are bonded together optionally with anodic bonding.

In an embodiment, there is presented a sensor wherein the analyte permeable membrane comprises, such as consists of, a polymer, such as an inorganic polymer, such as silicone, such as fluorosilicone.

In an embodiment, there is presented a sensor wherein the analyte permeable membrane enables separating liquids, such as aqueous solutions, on either side of the one or more analyte permeable openings.

In an embodiment, there is presented a sensor wherein the shortest distance from
  any point on the working electrode, through the one or more analyte permeable openings and the analyte permeable membrane to
  a point on an opposite side of the membrane with respect to the working electrode,
is equal to or less than 300 micrometer, such as equal to or less than 275 micrometer, such as equal to or less than 250 micrometer, such as equal to or less than 225 micrometer, such as equal to or less than 200 micrometer, such as equal to or less than 100 micrometer, such as equal to or less than 50 micrometer. A possible advantage of having this distance being relatively small may be that it enables reducing a response time of the sensor.

In an embodiment, there is presented a sensor wherein the shortest distance (239) from
  any point on the working electrode (104),
through the one or more analyte permeable openings (122) and the analyte permeable membrane (124) to
  a point on an opposite side of the analyte permeable membrane with respect to the working electrode (104),
is equal to or less than 100 micrometer. A possible advantage of having this distance being relatively small may be that it enables reducing a response time of the sensor.

In an embodiment, there is presented a sensor wherein the sensor comprises one or more additional electrodes, such as:
  a. A scavenger electrode, such as a scavenger electrode placed between the one or more analyte permeable openings and the working electrode,
  b. An additional working electrode in the reaction region, such as wherein the working electrode and the additional working electrode are placed between the one or more analyte permeable openings and the optional guard electrode, such as placed in parallel or in series with respect to a direction of movement of an analyte diffusing along the shortest possible path from the gas permeable opening to the working electrode.

A possible advantage of having a scavenger electrode (which may function in a similar manner to the optional guard electrode) placed between the one or more analyte permeable openings and the working electrode may facilitate that interfering substances from the associated volume may be rendered harmless in terms of the measurements at the working electrode by the scavenger electrode. A possible advantage of having an additional working electrode may be that one working electrode may be placed in front of the other (with respect to the one or more analyte permeable openings) and operated in a time-varying manner so that the signal on the other working electrode depends on the time-varying operation, so that the signal on the working electrode in combination with knowledge of the time-variation may be used to realize very low detection limits. Another possible advantage of having an additional working electrode may be that one working electrode may be placed in front of the other (with respect to the one or more analyte permeable openings), so that any signal on the other working electrode may be interpreted as an indication that a range linear detection of the first working electrode is exceeded. Another possible advantage of having multiple working electrodes may be that it enables measuring simultaneously different analytes (e.g., one type of analyte for each working electrode). In certain sensor embodiments it can be advantageous to place a scavenger chemical or electrode in a separate chamber in front of the analyte permeable membrane in order to remove an interfering species.

According to a second aspect of the invention, there is presented use of a sensor according to the first aspect for sensing an analyte in an associated volume.

According to an embodiment, there is presented use of the sensor wherein the analyte is sulfide. According to an embodiment, there is presented use of the sensor for measuring sulfide in a sewer and/or in waste water. According to an embodiment, there is presented use of the sensor for measuring sulfide in natural gas and/or biogas. According to an embodiment, there is presented use of the sensor for measuring sulfide in natural gas and/or biogas during a desulfurization process.

According to a third aspect of the invention, there is provided a method for producing a sensor according to the first aspect, comprising, such as comprising the following steps in that sequence:
  a. Adding liquid phase membrane material to the one or more analyte permeable openings,
  b. Removing a portion of membrane material (which may at this point be in liquid or solid form), such as by
    i. sawing it off,
    ii. wiping it off, such as wiping it off on the associated volume side,
    iii. grinding it off,
    iv. laser cutting.

An advantage of adding liquid phase membrane material and then removing a portion of the membrane material may be that it enables good control over the corresponding end of the (remaining) membrane material. Another possible advantage may be, that wafer dicing, e.g., by sawing, may contaminate the chamber if the membrane material is not there to keep contaminants (such as debris, sawdust, etc.) from entering into the chamber via the opening. It may be understood that when removing the portion of the membrane material, then the membrane material may (still) be in fluid or liquid form or it may have solidified. In some embodiments, a plurality of sensors is produced from a wafer which is split by dicing, where liquid phase membrane material is added to the one or more analyte permeable openings before dicing and where the portion of membrane material is removed in the dicing step. Wafer dicing may be understood to comprise sawing or laser cutting.

In an embodiment there is presented a method which further comprises solidifying the liquid phase membrane material.

The first, second and third aspect of the present invention may each be combined with any of the other aspects. These and other aspects of the invention will be apparent from and elucidated with reference to the embodiments described hereinafter.

BRIEF DESCRIPTION OF THE FIGURES

The electrochemical sensor according to the invention will now be described in more detail with regard to the accompanying figures. The figures show one way of implementing the present invention and is not to be construed as being limiting to other possible embodiments falling within the scope of the attached claim set.

DETAILED DESCRIPTION OF AN EMBODIMENT

Figure 1A:
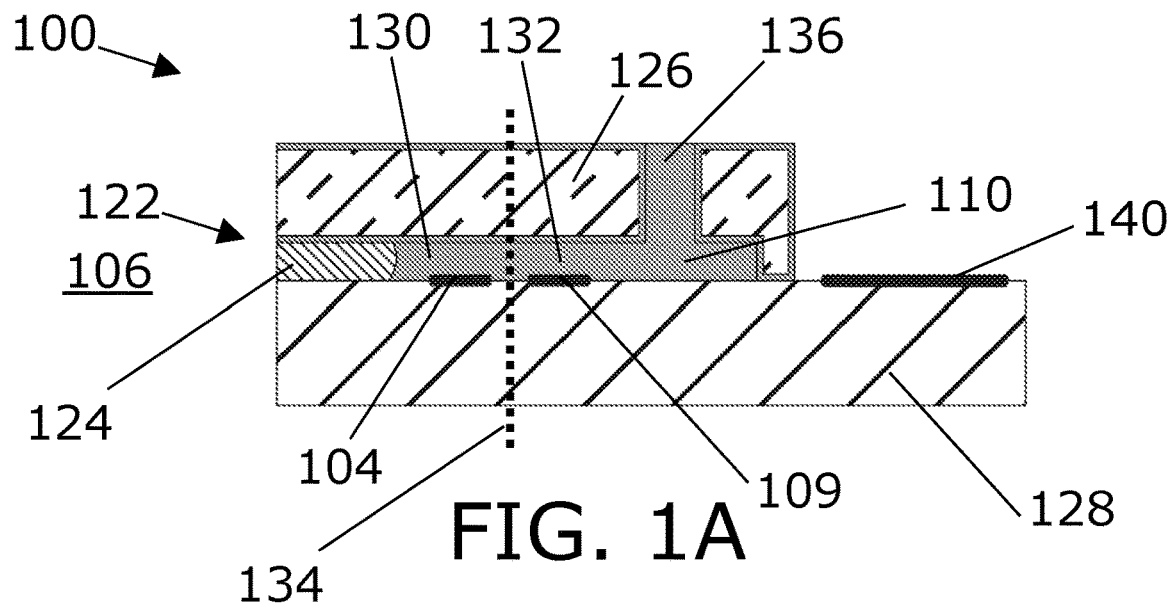
FIG. 1A depicts an electrochemical sensor for sensing an analyte.

FIG. 1A depicts an electrochemical sensor 100 for sensing an analyte in an associated volume 106, the sensor comprising
  a first solid element (126),
  a second solid element (128) being joined to the first solid element,
  a chamber (110) being placed at least partially between the first solid element and the second solid element, said chamber comprising
    a reaction region (130), and
    a reservoir region (132) being connected with the reaction region,
  wherein an analyte permeable opening (122) connects the reaction region (130) with the associated volume (106), such as said analyte permeable opening forming a diffusion barrier between the associated volume and the chamber, and wherein the electrochemical sensor (100) further comprises an analyte permeable membrane (124) in said analyte permeable opening, such as a silicone membrane, such as a membrane which enables separating liquids(such as aqueous solutions) on either side of the analyte permeable opening, a working electrode (104) in the reaction region, a reference electrode (108), and a guard electrode (109) arranged so as to enable reduction or oxidation of at least some reactants from at least a part of the reservoir region, such as reactants which could otherwise diffuse to the working electrode (104) and be reduced or oxidized at the working electrode, wherein the guard electrode comprises a thin film, such as a thin film placed on an inner wall of the chamber wherein the one or more analyte permeable openings are placed at least partially, such as fully, between the first solid element and the second solid element, and wherein the one or more analyte permeable openings are arranged so that a distance from any point in at least one cross-sectional plane to the nearest point of a wall of said opening is 25 micrometer or less, where said cross-sectional plane is orthogonal to a direction of movement of an analyte diffusing from the associated volume to the working electrode along the shortest possible path.

FIG. 1A furthermore shows an electrical connection pad 140 for electrical connection to the working electrode 104 and guard electrode 109, and an electrolyte opening 136 for filling of electrolyte into the cavity between the first and second solid elements. The dotted line 134 indicates the interface between reaction region 130 and reservoir region 132. The working electrode (104) is a thin film, and the working electrode and the guard electrode (109) are both placed on the second solid element (128). The first solid element (126) is joined to the second solid element (128) by anodic bonding and the first solid element is made from a silicon wafer. The second solid element comprises glass, such as Pyrex glass.

Figure 1B:
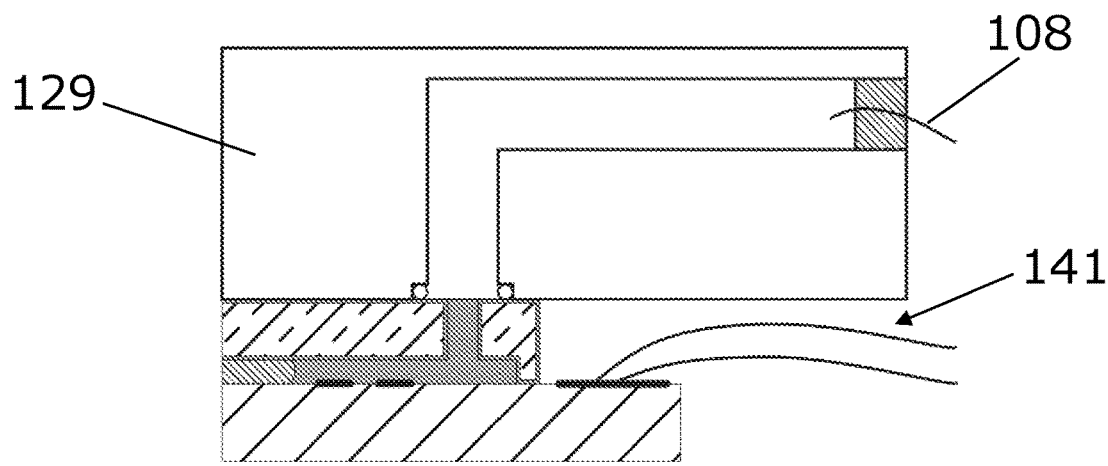
FIG. 1B shows the sensor with a third solid element.

FIG. 1B shows the sensor of FIG. 1A wherein an third solid element 129, such as part of a housing, has been placed adjacent to the first solid element, and forming fluid-tight interface between these elements by means of an O-ring. An advantage of this may be that the chamber may then be enlarged by being also partially confined by the third solid element, thus more electrolyte can be kept in the chamber, which in turn increases lifetime of the sensor. The figure furthermore shows electrical wires 141 connecting the electrical connection pad to peripheral electronics and a wire reference electrode 108 inserted as a wire in the third solid element 129. In another embodiment one or both of the working electrode 104 and the reference electrode comprise a thin film. For example, the reference electrode may instead of the wire reference electrode 108 be added as thin film electrode on the first and/or second solid element, which may be advantageous for simplifying production.

Figure 2:
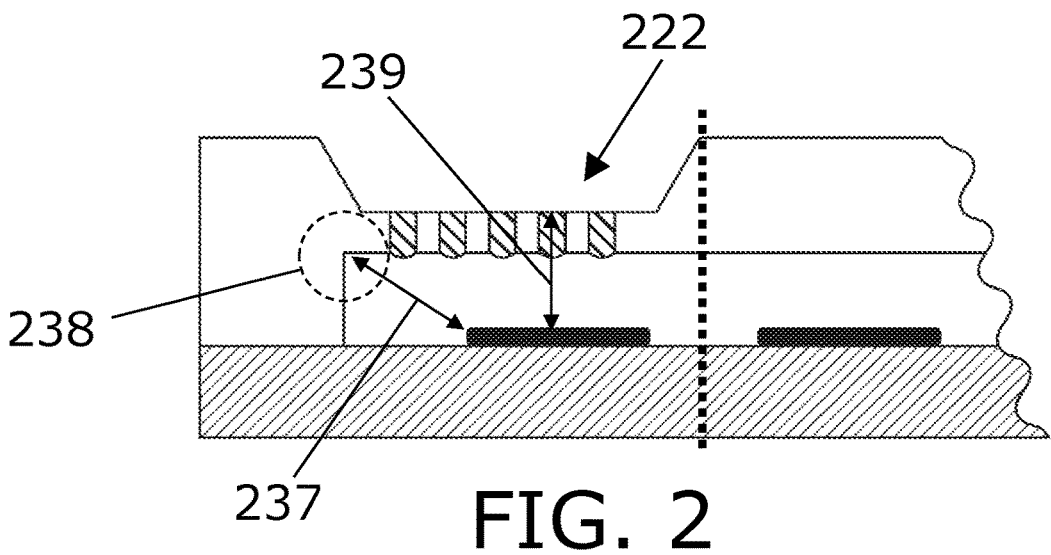
FIG. 2 shows a sensor with a plurality of analyte permeable openings.

FIG. 2 shows a sensor which comprises a plurality 222 of analyte permeable openings. The figure furthermore shows the analyte permeable openings being formed in one of the solid elements, which differs with respect to the embodiment depicted in FIGS. 1A-1B where the analyte permeable opening is formed at the interface between the first and second solid element.

FIG. 2 furthermore indicates a distance 237 between
the working electrode 104
and
a point 238 (such as encircled by the dashed circle 238) in the reaction region which is furthest away with respect to the working electrode is 500 micrometer or less, such as 250 micrometer or less, such as 100 micrometer or less, such as 50 micrometer or less, such as 25 micrometer or less, such as 10 micrometer or less, such as 5 micrometer or less.

FIG. 2 furthermore indicates that the shortest distance 239 from
any point on the working electrode 104, through the analyte permeable opening and the membrane to
a point on an opposite side of the membrane with respect to the working electrode, is equal to or less than 300 micrometer, such as equal to or less than 200 micrometer, such as equal to or less than 100 micrometer, such as equal to or less than 50 micrometer.

Figure 3:
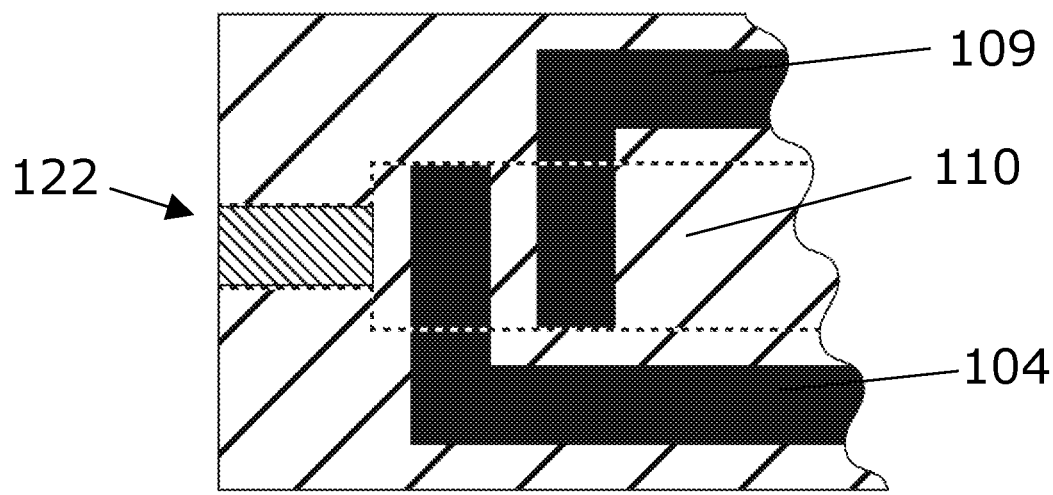
FIG. 3 shows a top-view of a sensor corresponding to the side view in FIG. 1A.

FIG. 3 shows a top-view of a sensor which corresponds to the side view depicted in FIG. 1A. In FIG. 3 the layout of the working electrode 104 and guard electrode 109 can be seen, and it can furthermore be seen that electrical connections may be integrated in the structure of the sensor outside of the chamber 110. Note that the dotted line denotes the position of the chamber (which may correspond to a cavity in the first and or second solid element), and the first and second solid element are forming a joining, such as bonding, interface outside the dotted line, such as encapsulating the thin film leads of the electrodes. In the present embodiments, the thin film of the electrodes is similar to the thin film of the leads, but the electrodes are exposed to the chamber whereas the leads are encapsulated in the sandwich structure of the first and second solid element. The length and width of the working electrode 104 in the chamber 110 in the present embodiment is 25 micrometer×100 micrometer, corresponding to an area covered of 2500 square micrometer. FIG. 3 thus depicts a sensor wherein an area covered, such as an area projected onto the wall of the chamber upon which it is placed, by the working electrode is equal to or less than 2500 square micrometers.

Figure 4:
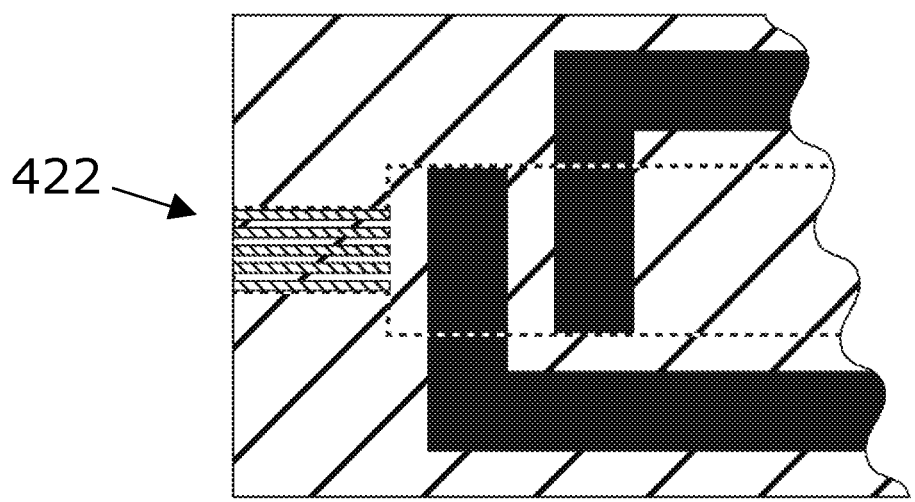
FIG. 4 shows a top-view with a plurality of analyte permeable openings.

FIG. 4 shows a top-view of a sensor similar to the top-view depicted in FIG. 3, except that the single analyte permeable opening 122 in FIG. 3 is replaced with a plurality 422 of analyte permeable openings.

Figure 5:
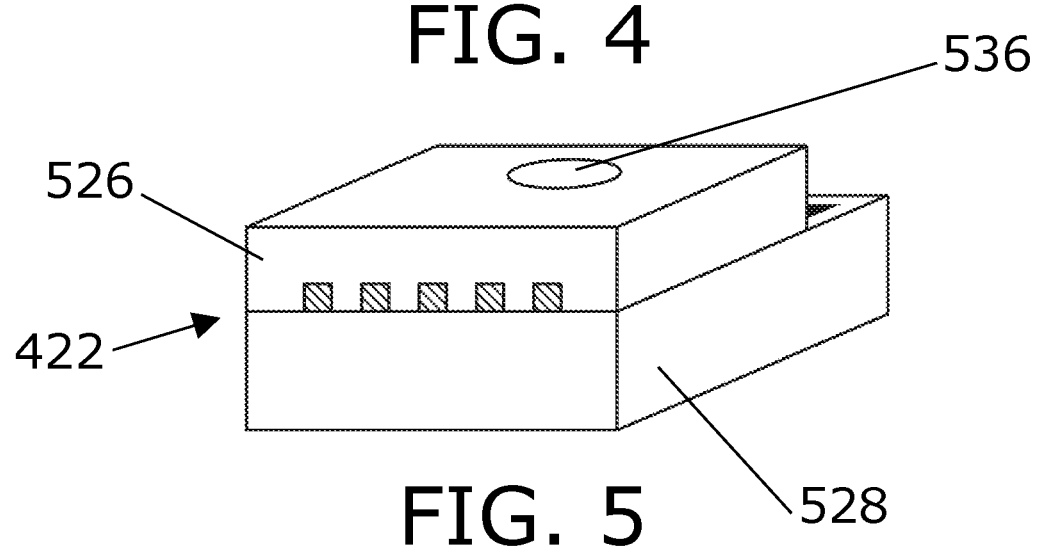
FIG. 5 shows a perspective view of a sensor.

FIG. 5 shows a perspective view of a sensor corresponding to the top-view depicted in FIG. 4, wherein cavities have been formed in first solid element 526 which cavities may the correspond to inter alia the plurality 422 of analyte permeable openings at the interface between the first and second solid elements when the first solid interface is joined to planar solid element 528. The figure also shows electrolyte opening 536, and a corner of an electrical connection pad is just visible on the second solid element behind the first solid element.

Figure 6:
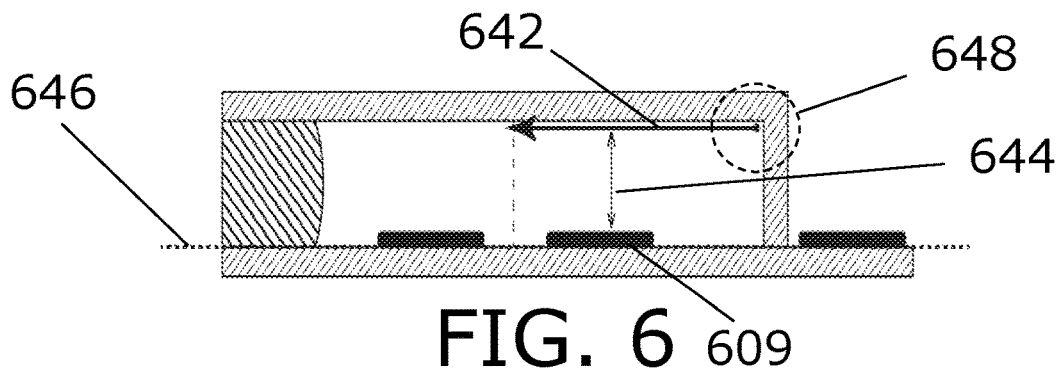
FIG. 6 illustrates movement of a substance.

FIG. 6 illustrates that a substance moving (as indicated by arrow 642), such as diffusing, from
the most distant part 648 (such as encircled by dashed circle 648) of
the reservoir region with respect to the reaction region, to any point in the reaction region,
would have to pass a point equal to or less than 100 micrometer away from the 20 guard electrode (said distance indicated by double-headed arrow 644), such 75 micrometer or less, such as 50 micrometer or less, such as 25 micrometer or less, such as 10 micrometer or less, such as 5 micrometer or less.

In generally applicable embodiments, there is presented a sensor wherein a substance moving from
- the most distant part (648) of the reservoir region (132) with respect to
- the reaction region (130),
- to
- any point in the reaction region,
- would have to pass a point equal to or less than 10 micrometer, such as 5 micrometer or less, away from the guard electrode.

FIG. 6 furthermore indicates that the guard electrode (609) is arranged so that an electrolyte conductance between working electrode and reference electrode is substantially similar, such as similar, for the sensor compared to a similar sensor wherein the guard electrode has been removed. Since the guard electrode is implemented as a thin film electrode, which occupies substantially no volume, it enables that the cross-sectional area—which is related to and increases with the electrolyte conductance between working electrode and reference electrode—can be kept relatively high, which in turn enables continuously having a sufficient electrolyte supply, such as ions in the electrolyte, to the working electrode from the reservoir region.

FIG. 6 furthermore indicates that a plane 646 may be defined which is parallel with and tangential with a boundary wall of each of:
- The reaction region,
- The reservoir region,
- The analyte permeable opening.

Figure 7:
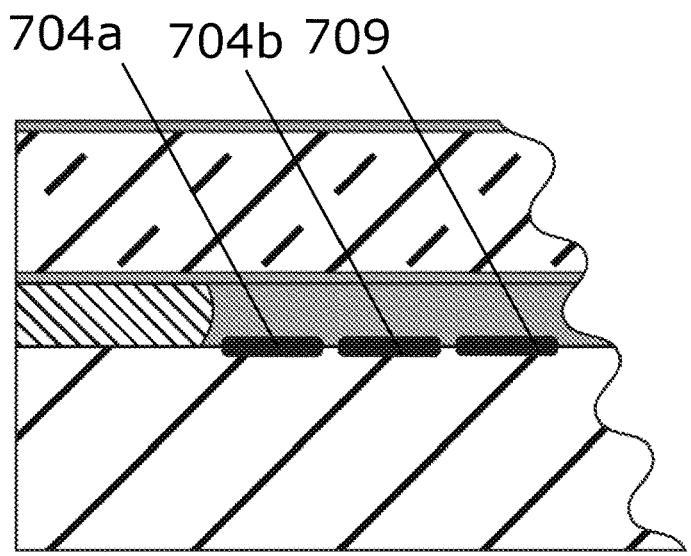
FIG. 7 depicts a sensor comprising an additional electrode.

FIG. 7 depicts a sensor comprising an additional electrode 704a placed between the analyte permeable opening and the working electrode 704b. A guard electrode 709 is also depicted in FIG. 7.

Figure 8:
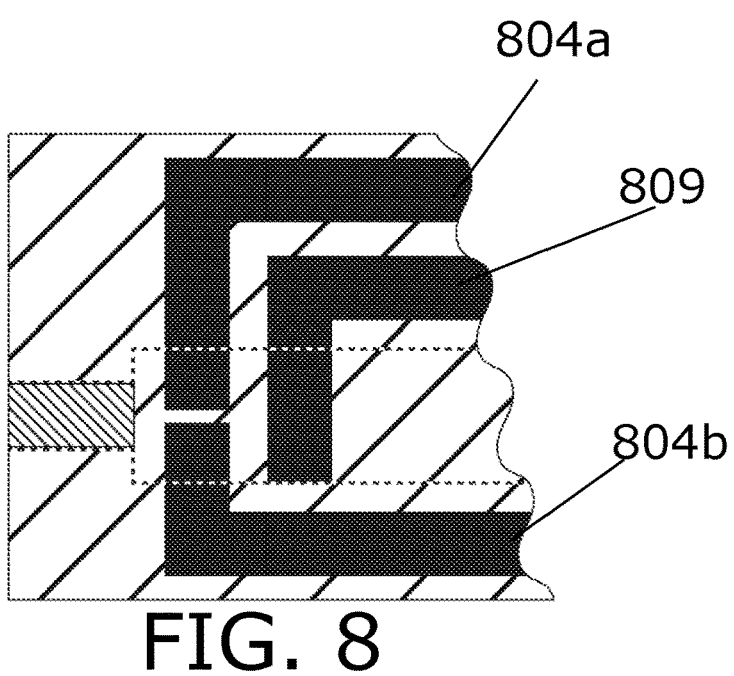
FIG. 8 depicts an additional working electrode.

FIG. 8 depicts working electrode 804a and an additional working electrode 804b in the reaction region, wherein the working electrode and the additional working electrode are placed between the analyte permeable opening and the guard electrode. In FIG. 8 they are placed in parallel, but they could also be placed in series (similar to electrodes 704a-b in FIG. 7) with respect to a direction of movement of an analyte diffusing along the shortest possible path from the analyte permeable opening to the working electrode. A guard electrode 809 is also depicted in FIG. 8.

Figure 9:
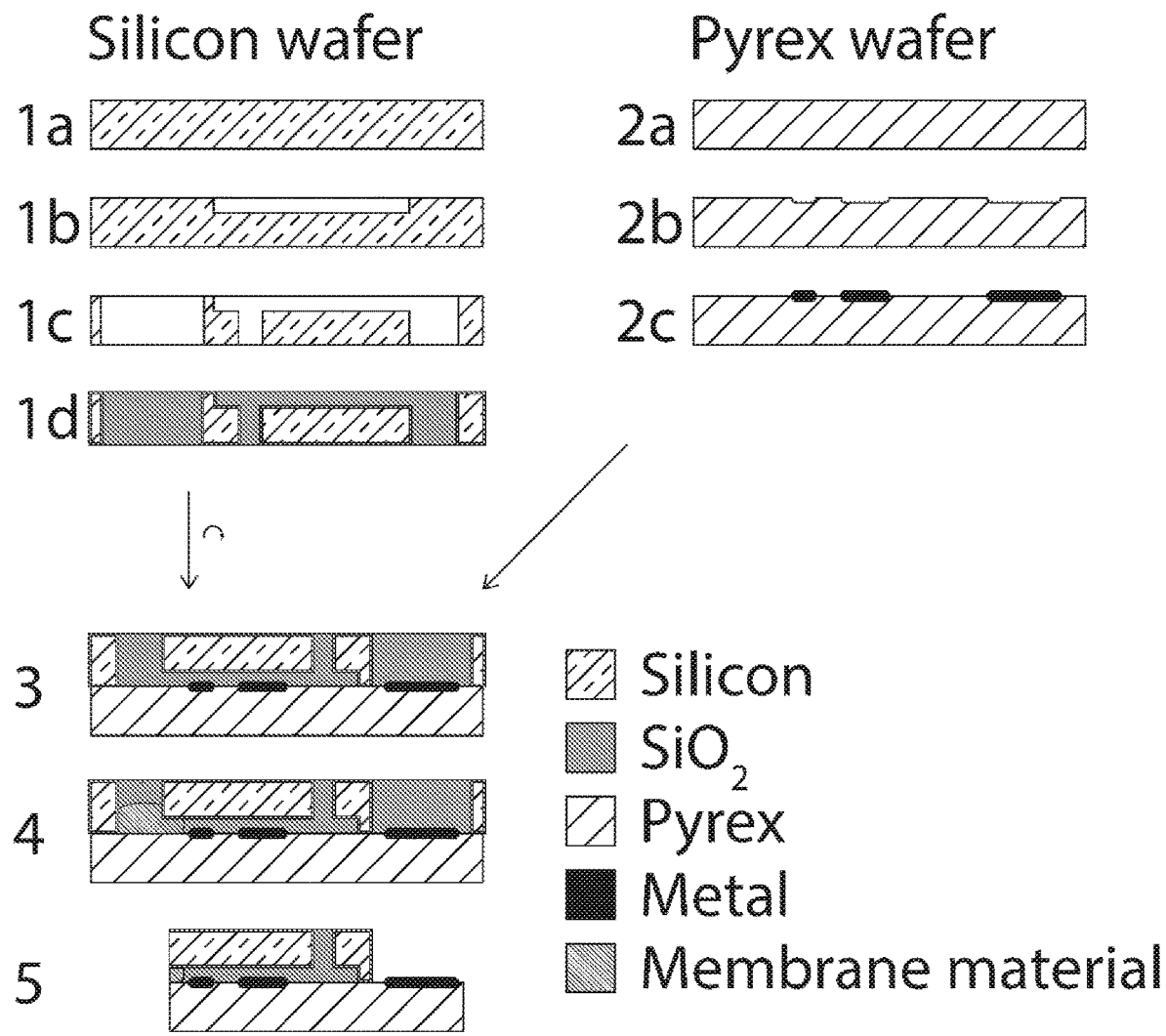
FIGS. 9-10 illustrate a detailed process of manufacturing a sensor
Figure 10:
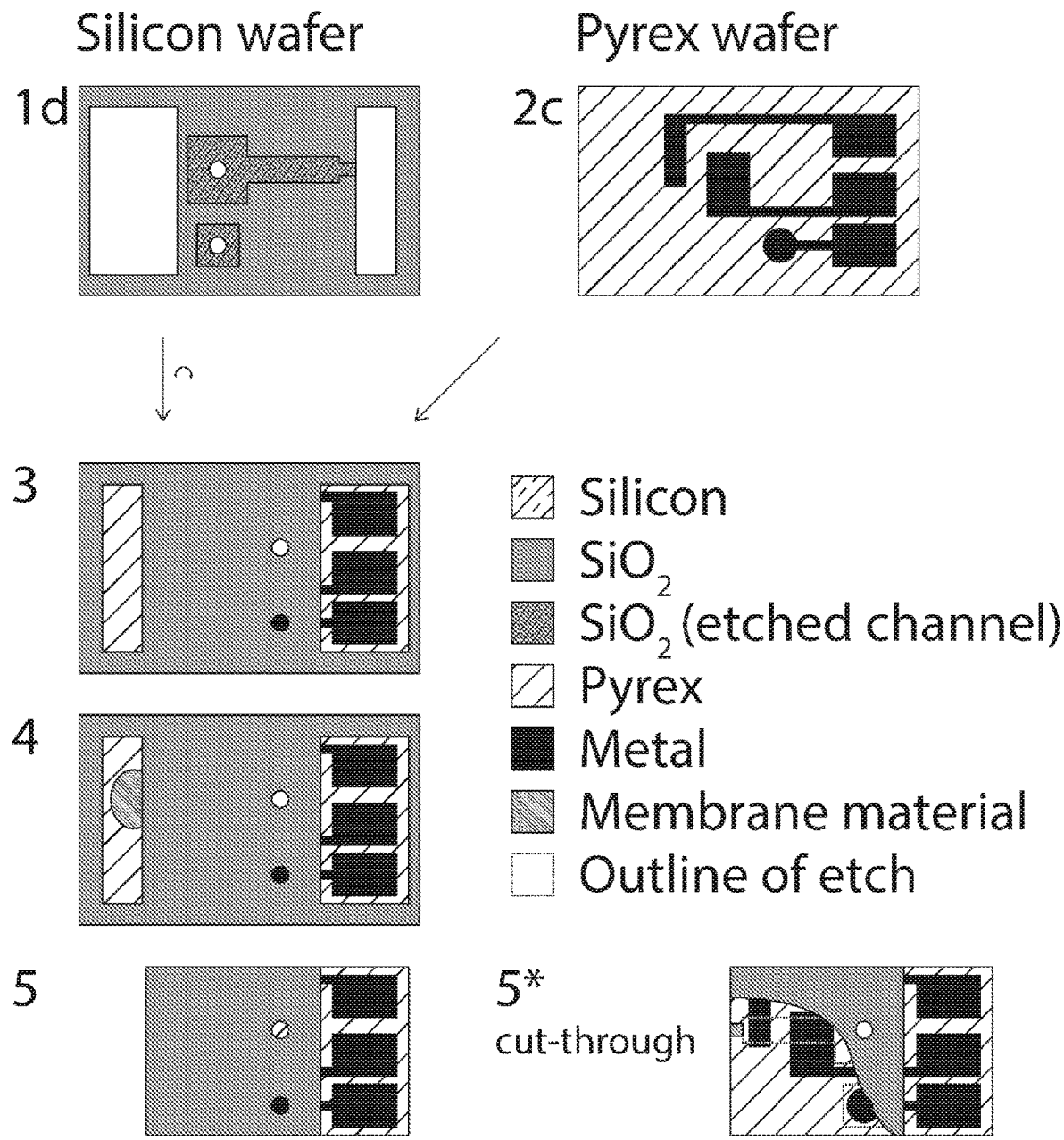

FIGS. 9-10 illustrate a detailed process of manufacturing a sensor according to an embodiment of the invention.

FIG. 9 comprises side views.

FIG. 10 comprises top-views.

In step 1a the cavities are etched in a silicon wafer (<100>, 4-inch, 350 micrometer, double side polished). First, the Si wafer is treated in buffered hydrogen fluoride (BHF) for 30 seconds. In step 1b a 1.5 um AZ5214e Novolac resist is spun on the wafer and a part of the chamber is etched anistropically 5 micrometer into the Si by deep reactive-ion etching (DRIE). In step 1c thereafter, through-holes are etched using the same method, but using 10 micrometer resist. The wafer was attached to a carrier wafer using Krystal bond™ before performing the deep etch. In step 1d an insulating layer of 100 nm SiO2 is formed by thermal oxidation. In step step 2a-2c 100 nm Pt thin-film electrodes are deposited on a Pyrex wafer using 2.2 micrometer AZ5214e Novolac as image-reversal as lift-off resist. Before physical vapor deposition of Pt, the same areas may optionally (step 2b) be etched by 50 micrometer in BHF to recess the electrodes. 2 nm Ti is deposited before Pt to increase the adhesion. In step 3 the Si wafer and the Pyrex wafer are joined by anodic bonding at 350° C. using 600 volts. In step 4 the silicone membrane material is filled into the channels and cured. In step 5 the wafers as diced with blue foil covering the openings in the Si wafer. After dicing the chip is attached to an external electrolyte chamber in which the reference electrode wire is placed. The device is filled with electrolyte. Remaining air bubbles are removed by incubation/boiling in vacuum at room temperature.

Figure 11:
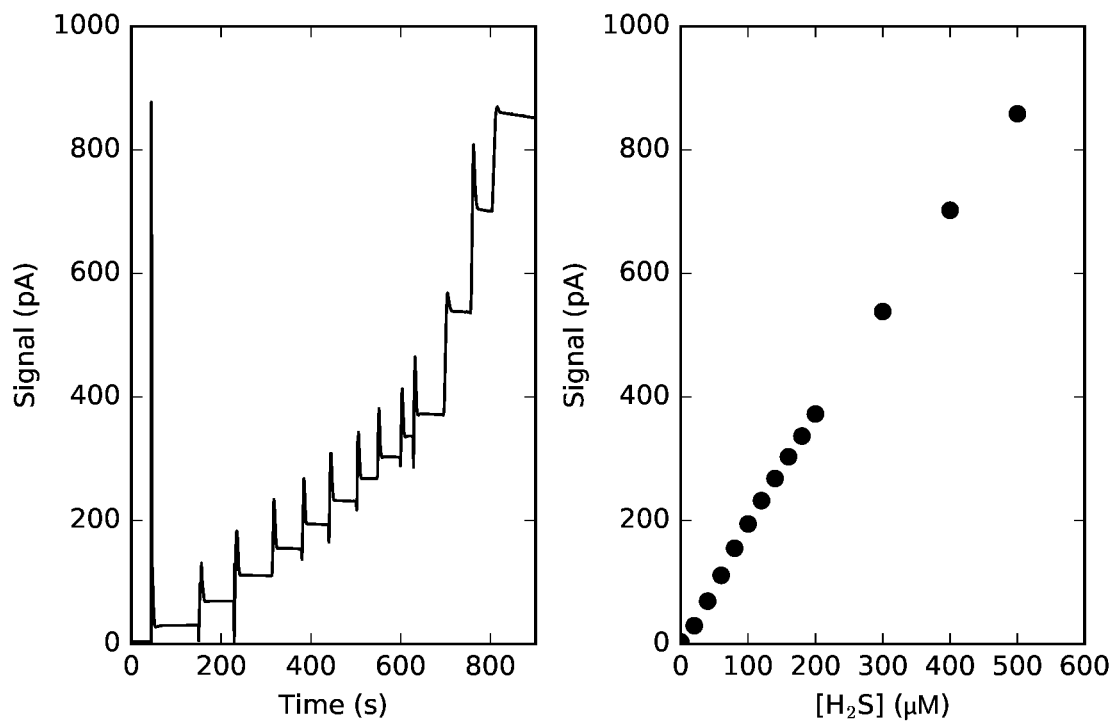
FIG. 11-12 shows signals as obtained with a sensor.

FIG. 11 shows in the left figure a signal as obtained with a sensor according to an embodiment of the invention as a function of time, where a concentration of $H_2S$ in the associated volume has been increased in steps (the steps corresponds to 10 additions of 20 micromolar and subsequently 3 additions of 100 micromolar). In the right figure, the signal is plotted as a function of the $H_2S$ concentration in the associated volume. It may be derived from the signal that a response time of the sensor is approximately 3 seconds (corresponding to the time it takes from the change in analyte concentration in the associated volume is increased in a step function and until the signal reaches 90% of its final settled value). In other embodiments the response time may be lower, such as 0.3 seconds, such as 0.1 second.

Figure 12:
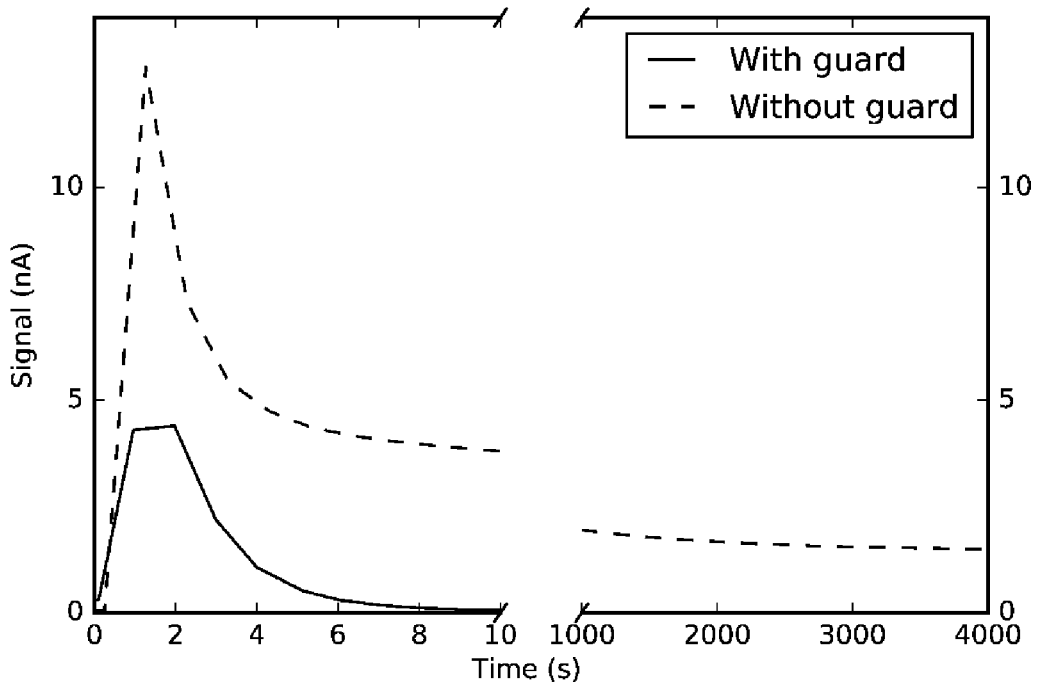

FIG. 12 shows start-up signals as obtained with a sensor according to an embodiment of the invention as a function of time, respectively, with and without the guard electrode being employed for electrochemical reactions. It may be seen that the presence of the guard electrode enables rapidly achieving a low-base line signal.

Figure 13:
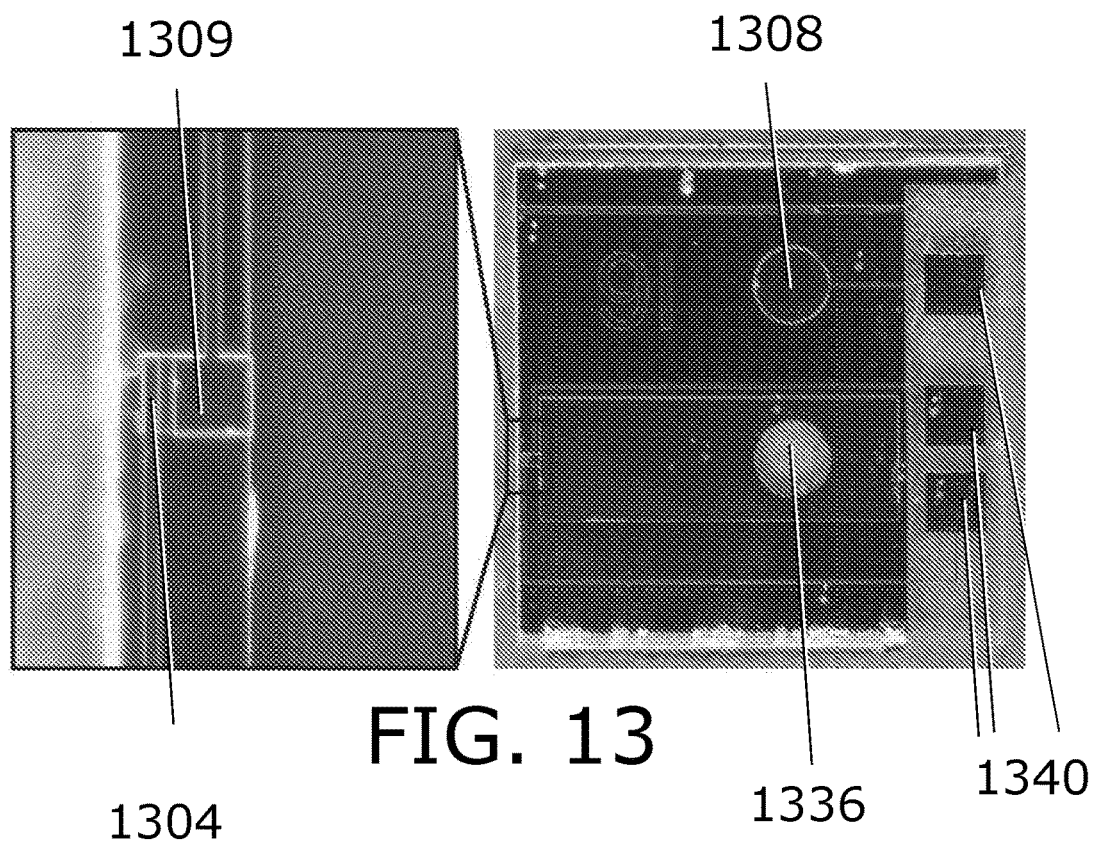
FIGS. 13-14 shows (light) microscope images of a sensor.

FIG. 13 shows a (light) microscope image of a sensor corresponding in the left figure (which is magnification of the right figure) to the top view seen, e.g., in schematic FIG. 3, where the working electrode 1304 and guard electrode 1309 can be seen. In the right figure, also electrolyte opening 1336 and electrical connection pads 1340 are indicated. In the right side figure, an on-chip reference electrode 1308 is depicted. A trough-going hole is placed in the silicon above the circular part of the electrode.

Figure 14:
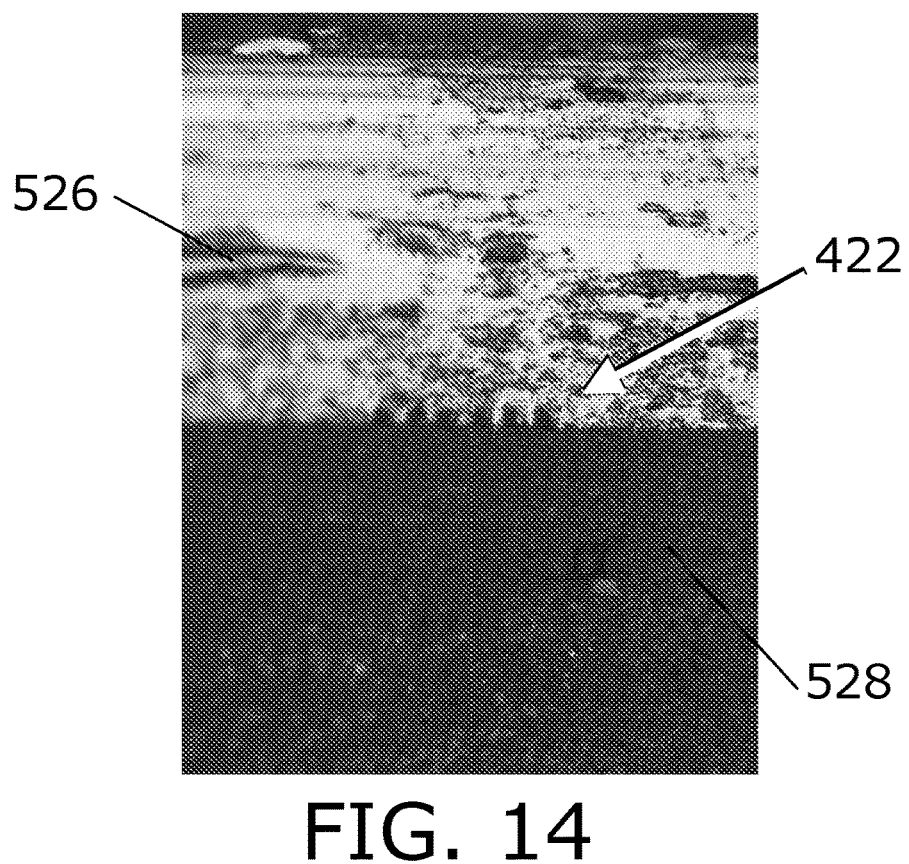

FIG. 14 shows a (light) microscope image of an end of the sensor corresponding to the end with the plurality of analyte permeable openings 422 in FIG. 5. The image furthermore shows the first solid element 526 and the second solid element 528.

Figure 15:
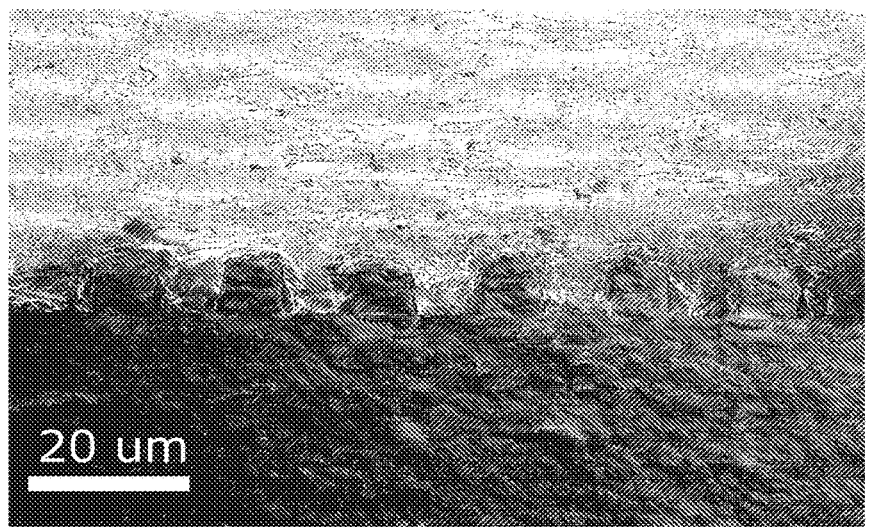
FIGS. 15-16 shows scanning electron microscope (SEM) images.

FIG. 15 shows a scanning electron microscope (SEM) image similar to the (light) microscope image in FIG. 14.

Figure 16:
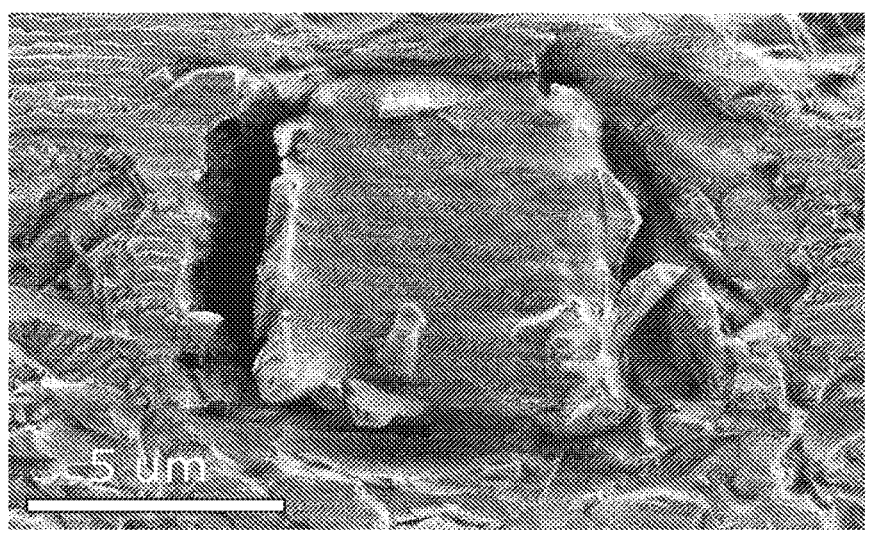

FIG. 16 is another SEM image similar to the image in FIG. 15, but with higher magnification. The analyte permeable openings and the analyte permeable opening imaged comprises a silicone membrane.

Figure 17:
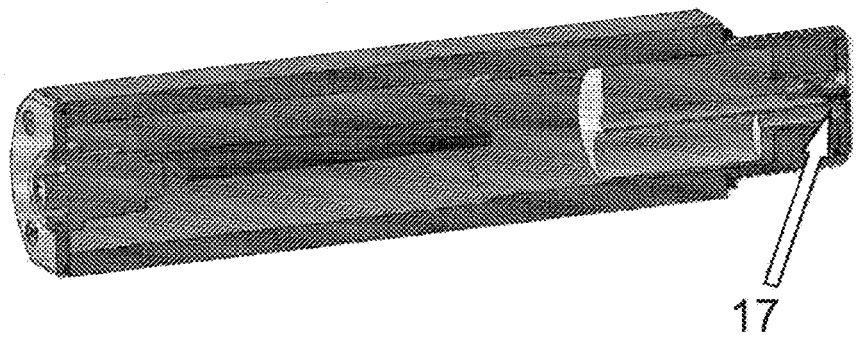
FIG. 17 shows the first and second solid with a third solid element.

FIG. 17 shows an embodiment wherein the first and second solid elements are integrated in a third solid element with a larger volume for enlarging the chamber (with respect to a volume of the chamber between the first and second solid elements). The first and second solid element joined together is indicated by the arrow 17, and inserted in a housing with a printed circuit board and connections for power and data transmission. The printed circuit board contains a voltage source and a current meter sensitive to currents in the range of picoamperes.

Figure 18:
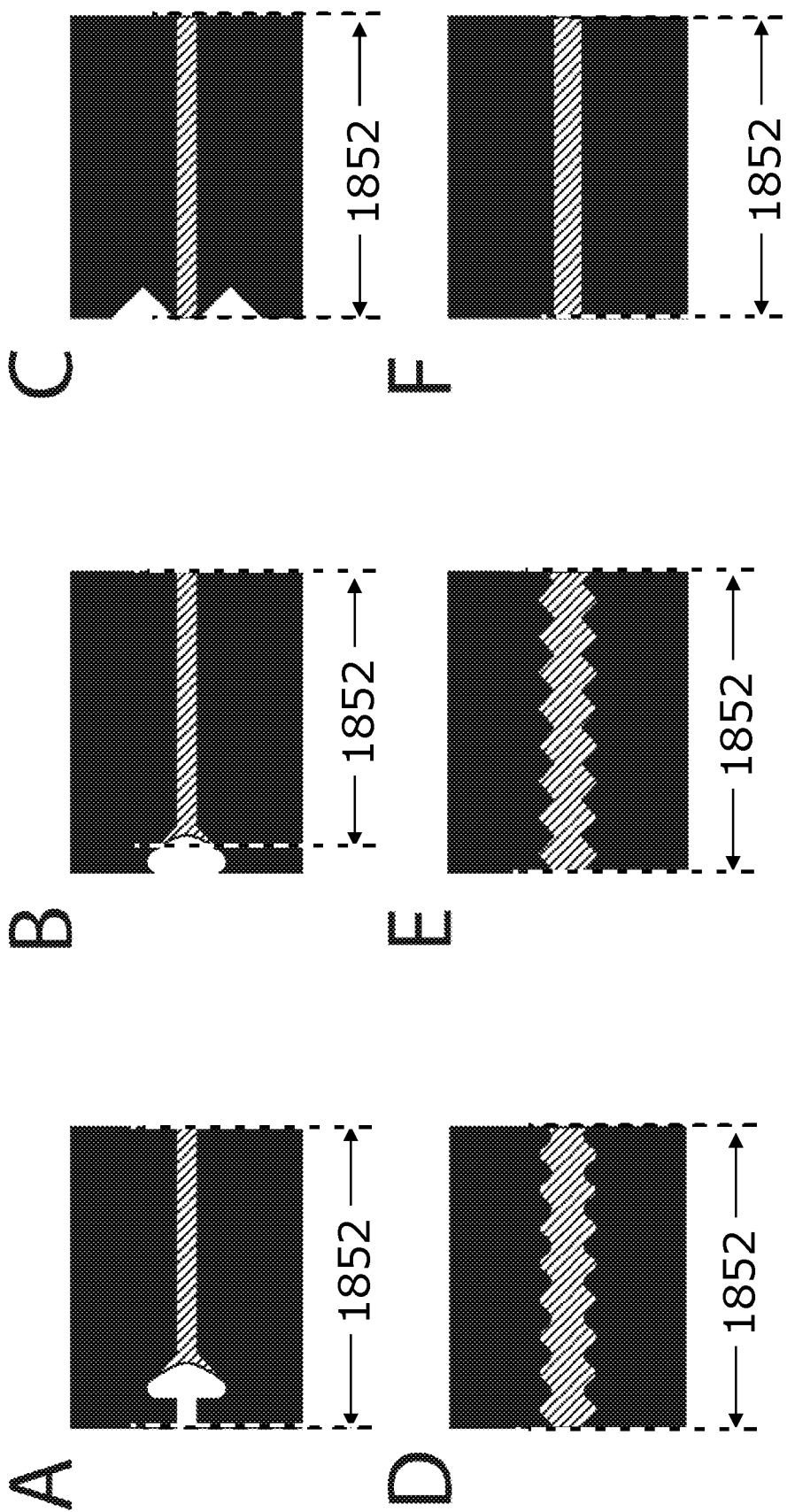
FIG. 18 shows schematic drawing of 6 different types of analyte permeable openings FIG. 19 show microscope images of the analyte permeable openings corresponding to the schematics of FIG. 18.

FIG. 18 shows schematic drawing of 6 different types of analyte permeable openings, where the openings are each understood to separate an associated volume on the right side and a chamber on the left side. The hatched areas indicate the analyte permeable membrane, which is each case could be placed there via capillary filling (from right to left). A length 1852 of each analyte permeable opening is indicated in each subfigure.

FIG. 18 also shows (for example in subfigures D and E) embodiments wherein one or more or all boundary walls of the one or more analyte permeable openings have a non-rectilinear shape, such as a curved (for example subfigure D) or piecewise rectilinear shape, such as a zig-zag shape (for example subfigure E), such as wherein the one or more analyte permeable openings has different cross-sectional areas at different positions (for example subfigures A, D and E).

Figure 19:
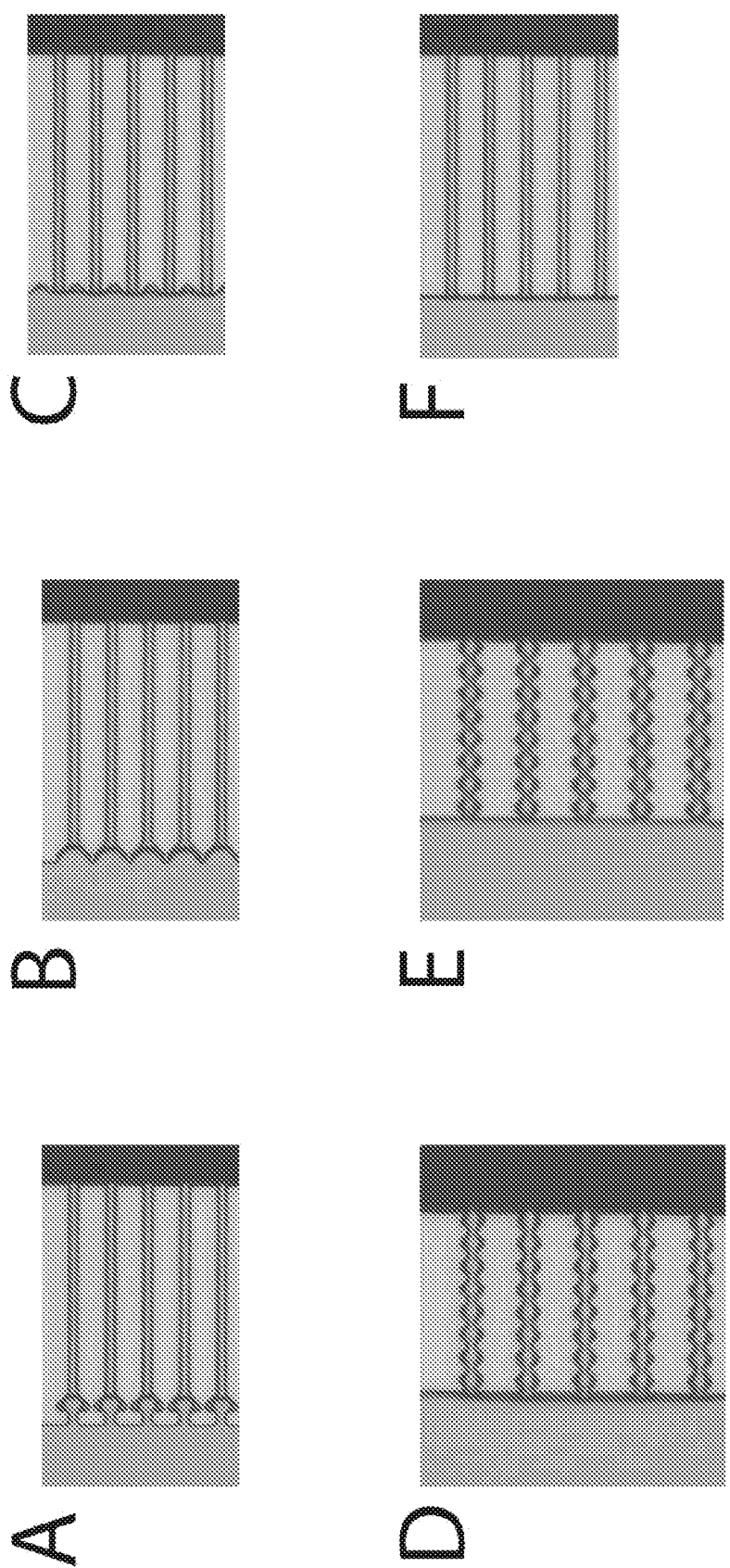

FIG. 19 show microscope images of the analyte permeable openings corresponding to the schematics of FIG. 18. In each image there are 5 parallel analyte permeable openings. The width (i.e., the size of the opening from wall-to-wall in the plane of the paper in a direction orthogonal to a flow direction through the opening) of each analyte permeable opening is 5 micrometer for A, B, C, and F and 2 micrometers for D and E. The length is 100 micrometers for A, B, C, and F and 50 micrometers for D and E. The analyte permeable membrane material has been placed in liquid form on the right hand side of each opening, and then filled the opening via capillary filling until a position at the end of the analyte permeable opening and/or at a kink within the analyte permeable opening. It may be noted that widths of 2 micrometer may also be possible and may yield improved results in terms of capillary filling and stopping of the membrane material at the end of each opening.

Figure 20:
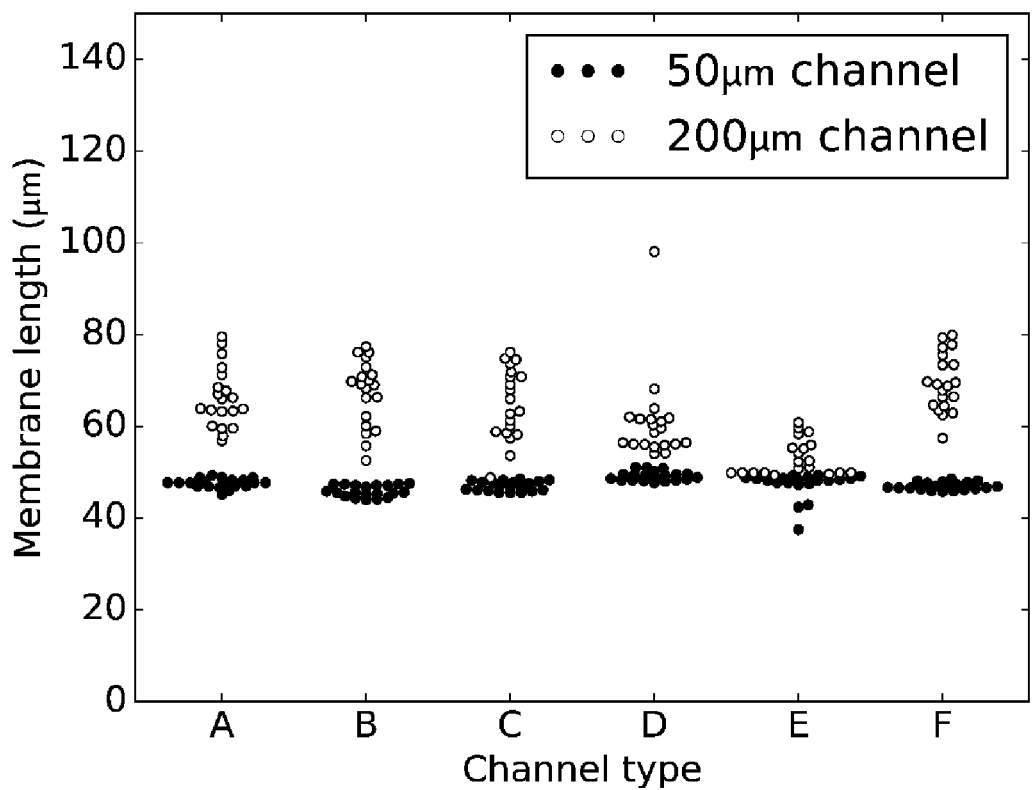
FIGS. 20-21 shows data for length of the analyte permeable membrane as deposited directly from a tube with liquid analyte permeable membrane material.

FIG. 20 shows data for length of the analyte permeable membrane as deposited directly from a tube with liquid analyte permeable membrane material (being Dow Corning 734 at 24 degrees C.) into etched channels, i.e., placed on the right hand side of the openings with shapes as depicted in FIGS. 18-19. Depth of openings (etch depth) are 5 micrometer and the width of each of the channels is 2 micrometer. Data is shown as a swarmplot for two different analyte permeable opening lengths (50 micrometer and 200 micrometer). The analyte permeable membrane material is stopped (i.e., capillary filling until a position) at the end of the opening or at a kink within the opening for the 50 micrometer openings. However, for the 200 micrometer openings, it continues. The different openings types are named A-F corresponding to the opening types illustrated in FIGS. 18-19.

Figure 21:
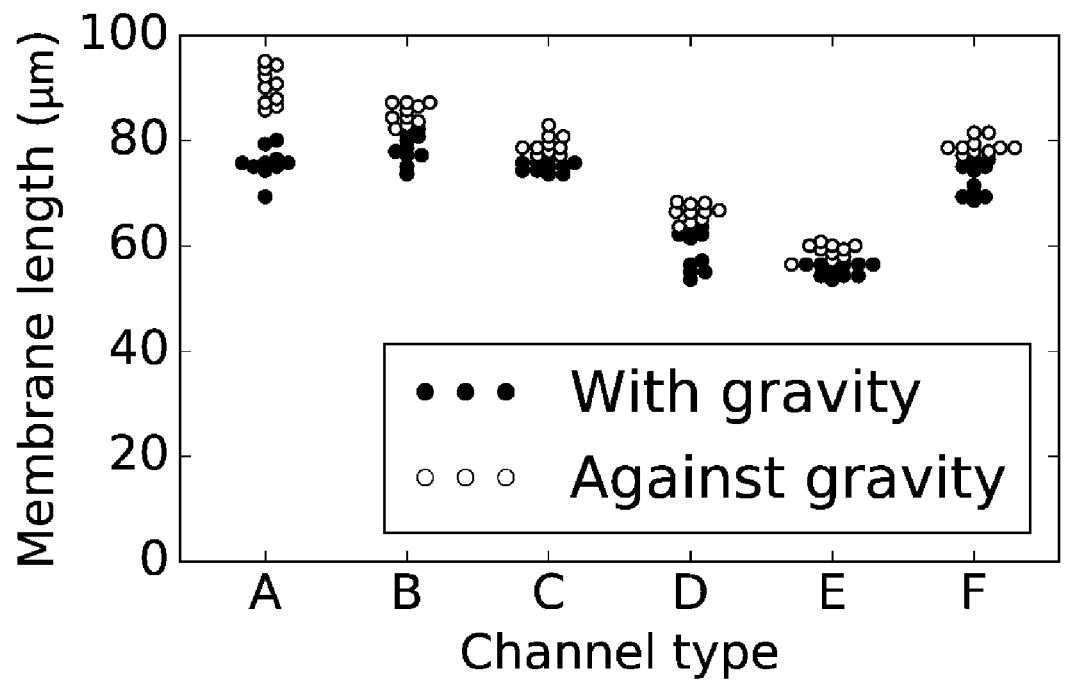

FIG. 21 shows data for length of the analyte permeable membrane as deposited directly from a tube with liquid analyte permeable membrane material (being Dow Corning 734 at 24 degrees C.) into etched channels, i.e., placed on the right hand side of the openings as depicted in FIGS. 18-19. Depth of openings (etch depth) are 5 micrometer and the width of each of the channels is 2 micrometer. Data is shown as a swarmplot for openings where the liquid material is placed at a bottom (with respect to gravity) of openings pointing vertically upwards and at the top (with respect to gravity) of openings pointing vertically downwards, i.e., the capillary filling works with and against gravity respectively. The analyte permeable membrane material comes to and stops at similar position in both cases indicated that gravity is insignificant and that the capillary force is the driving force behind filling of the openings with liquid analyte permeable membrane material. The different openings types are named A-F corresponding to the opening types illustrated in FIGS. 18-19.

Thus, FIGS. 20-21 demonstrates for a wide variety of opening types that capillary filling is possible and that the capillary filling furthermore enables stopping of the membrane at a predetermined position.

Figure 22:
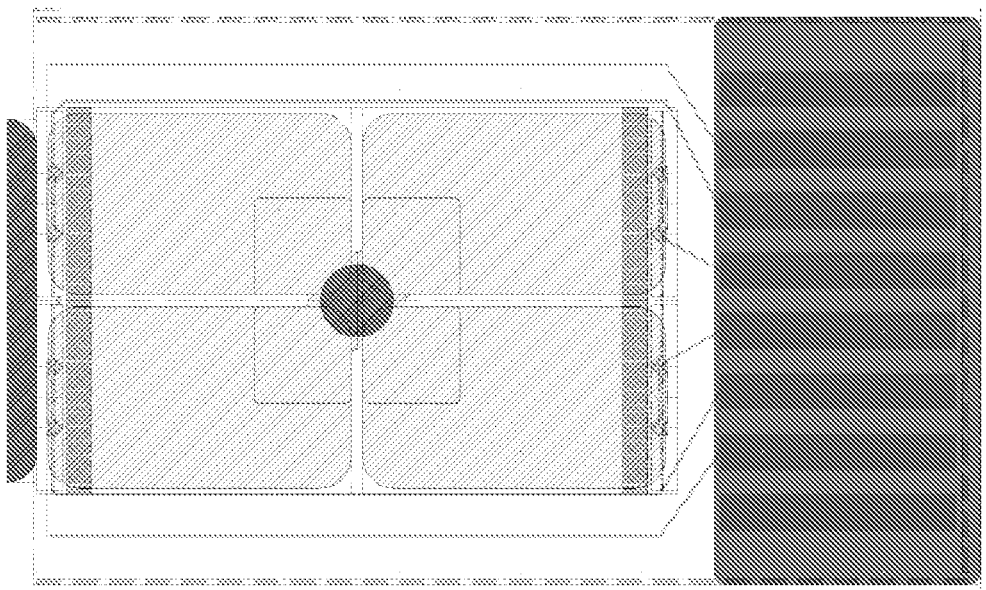
FIG. 22 shows schematic drawing of embodiment with multiple working electrodes.

FIG. 22 shows a schematic drawing of embodiment with multiple working electrodes. The left hand side shows inlets with multiple working electrodes (4 pairs of two sequentially arranged working electrodes) and a guard electrode. The right hand side shows working electrodes in compartments with no inlets, which working electrodes can be used to track non-analyte related effects, such as noise, temperature and stability. The left hand side inlets (4 inlets) may have similar membrane lengths to ensure easy comparison (if everything is in order, the signals should then be similar for sensors at different openings) or different legnths, for example the upper compartment may have relatively short membranes in the openings and the the lower compartment may have relatively long membranes in the openings (where 'relatively' refers to the other compartment of upper and lower), which may ensure longer lifetime.

Figure 23:
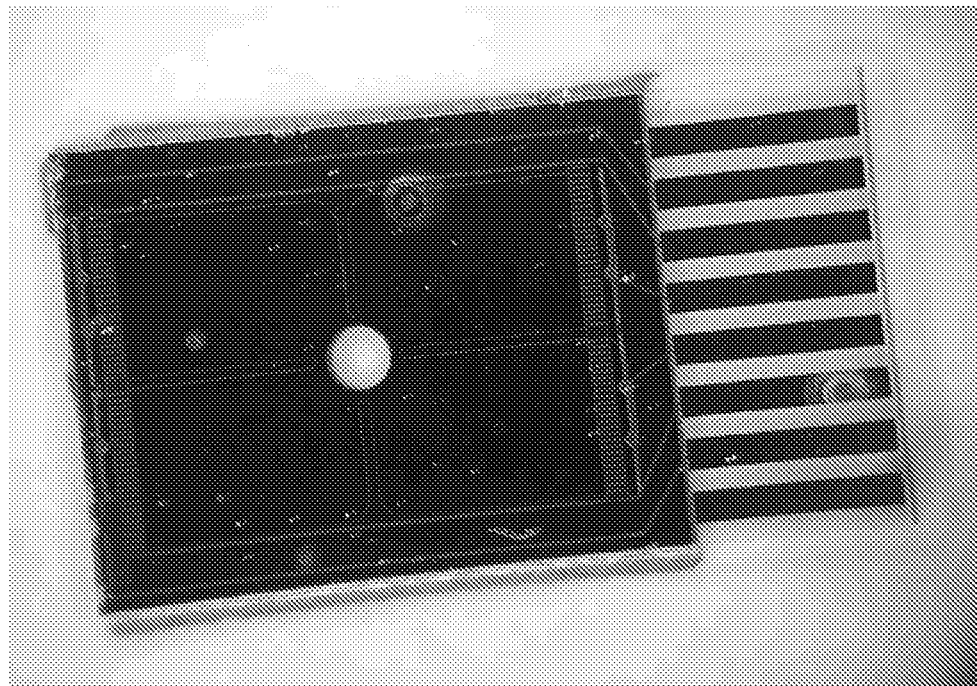
FIG. 23 shows image of embodiment with multiple working electrodes.

FIG. 23 shows an image of embodiment with multiple working electrodes (such as corresponding to the schematic in FIG. 22).

In embodiments E1-E15 of the invention, there is presented:

E1. A electrochemical sensor (100) for sensing an analyte in an associated volume (106), the sensor comprising
  a first solid element (126),
  a second solid element (128) being joined to the first solid element,
  a chamber (110) being placed at least partially between the first solid element and the second solid element,
  a working electrode (104) in the chamber (110),
  a reference electrode (108), and
  wherein one or more analyte permeable openings (122) connect the chamber with the associated volume (106) and wherein the electrochemical sensor (100) further comprises
  an analyte permeable membrane (124) in said one or more analyte permeable openings,
  and wherein the one or more analyte permeable openings are arranged so that a distance from any point in at least one cross-sectional plane to the nearest point of a wall of said opening is 25 micrometer or less, where said cross-sectional plane is orthogonal to a direction of movement of an analyte diffusing from the associated volume to the working electrode along the shortest possible path.

E2. A sensor (100) according to any one of the preceding embodiments, wherein the analyte permeable membrane material could have been placed in the one or more analyte permeable openings (122) by filling via a capillary force.

E3. A sensor (100) according to embodiment E2, wherein said one or more analyte permeable openings (122) and/or said chamber (110) is further arranged so that the capillary force is so low at a position that said capillary force could not drive said analyte permeable membrane material past said position.

E4. A sensor (100) according to any one of the preceding embodiments, wherein for at least one of the one or more analyte permeable openings the end of the analyte permeable membrane (124) which faces the chamber is placed at
  a. the end of the at least one of the one or more analyte permeable openings (122) which faces the chamber,
  b. a position where at least one boundary surface of at the least one of the one or more analyte permable openings (122) presents a kink, and/or
  c. a position wherein an entity given as $(1/A)*dA/dz$ is equal to or larger than 1/micrometer, wherein A is area of a cross-section of the at least one of the one or more of analyte permeable openings (122), said cross-section being orthogonal to a path through the at least one of the one or more analyte permeable openenings, and z is a position along the path through the at least one of the one or more analyte permeable openings.

E5. A sensor (100) according to any one of the preceding embodiments, wherein one or more or all boundary walls of the one or more analyte permeable openings (122) have a non-rectilinear shape.

E6. A sensor (100) according to any one of the preceding embodiments, wherein an angle between a boundary wall of the one or more analyte permeable openings (122) at the end of the one or more analyte permeable openings which faces the chamber and an abutting wall of the chamber is more than 270 degrees.

E7. A sensor according to any one of the preceding embodiments, wherein
 a. the analyte permeable membrane (124) is a polymer,
 b. the analyte permeable membrane (124) is passive,
 c. the analyte permeable membrane (124) is selective to non-ionic substances.

E8. A sensor (100) according to any one of the preceding embodiments, wherein the chamber comprises:
 a reaction region (130), and
 reservoir region (132) being connected with the reaction region,
and wherein the electrochemical sensor (100) further comprises
 a guard electrode (109) arranged so as to enable reduction or oxidation of at least some reactants from at least a part of the reservoir region, wherein the guard electrode comprises a thin film.

E9. A sensor (100) according to any one of the preceding embodiments, wherein the one or more analyte permeable openings (122) are placed at least partially between the first solid element (126) and the second solid element (128).

E10. A sensor (100) according to any one of the preceding embodiments, wherein the sensor comprises a plurality (422) of analyte permeable openings.

E11. A sensor (100) according to any one of the preceding embodiments, wherein one or both of:
 The working electrode (104), and
 The reference electrode (108),
comprise a thin film.

E12. A sensor (100) according to any one of the preceding embodiments, wherein a distance (237) between
 the working electrode (104)
and
 a point (238) in the reaction region which is furthest away with respect to the working electrode
is 500 micrometer or less,
and/or
wherein an area covered by the working electrode (104) is equal to or less than 2500 square micrometer,
and/or
wherein the shortest distance (239) from
 any point on the working electrode (104),
through the one or more analyte permeable openings (122) and the analyte permeable membrane (124) to
 a point on an opposite side of the analyte permeable membrane with respect to the working electrode,
is equal to or less than 300 micrometer.

E13. A method for producing a sensor (100) according to any one of the preceding embodiments, comprising:
 a. Adding fluidic membrane material to the one or more analyte permeable openings (122),
 b. Removing a portion of membrane material, such as by
  i. sawing it off,
  ii. wiping it off,
  iii. grinding it off,
  iv. laser cutting.

E14. A method according to embodiment E13, wherein the method further comprises solidifying the liquid phase membrane material.

E15. Use of a sensor (100) according to any one of embodiments E1-E12 for sensing an analyte in an associated volume.

For the above embodiments E1-E15, it may be understood that reference to preceding 'embodiments' may refer to preceding embodiments within embodiments E1-E15. It may furthermore be understood that any of the embodiments E1-E15 may be combined with any other embodiment disclosed in this application.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. An electrochemical sensor for sensing an analyte in an associated volume, the sensor comprising:
 a first solid element,
 a second solid element being joined to the first solid element,
 a chamber being placed at least partially between the first solid element and the second solid element,
 a working electrode in the chamber,
 a reference electrode, and
 wherein one or more analyte permeable openings connect the chamber with the associated volume and wherein the electrochemical sensor further comprises:
 an analyte permeable membrane in said one or more analyte permeable openings, wherein the membrane is not permeable to ions,
 wherein the one or more analyte permeable openings are configured such that a distance from any point in at least one cross-sectional plane to the nearest point of a wall of said opening is 25 micrometer or less, wherein said cross-sectional plane is orthogonal to a direction of movement of an analyte diffusing from the associated volume to the working electrode along the shortest possible path, and
 wherein the electrochemical sensor is configured to detect at least one analyte selected from the group consisting of nitrous oxide ($N_{2O}$), hydrogen sulfide ($H_2S$), hydrogen ($H_2$), and nitric oxide (NO).

2. The sensor according to claim 1, wherein the shortest distance from
 any point on the working electrode,
 through the one or more analyte permeable openings and the analyte permeable membrane to
 a point on an opposite side of the analyte permeable membrane with respect to the working electrode,
is equal to or less than 100 micrometer.

3. The sensor according to claim 1, wherein the analyte permeable membrane material is configured to be placed in the one or more analyte permeable openings by filling via a capillary force.

4. The sensor according to claim 1, wherein said chamber is comprising an electrolyte solution.

5. The sensor according to claim 4, wherein the electrolyte solution is a liquid comprising charge carriers in the form of dissolved ionic compounds.

6. The sensor according to claim 1, wherein the membrane enables separating liquids on either side of the one or more analyte permeable openings.

7. The sensor according to claim 1, wherein the membrane forms a hydrophobic barrier.

8. The sensor according to claim 1, wherein:
a. the analyte permeable membrane is a polymer,
b. the analyte permeable membrane is passive, or
c. the analyte permeable membrane is selective to non-ionic substances.

9. The sensor according to claim 1, wherein the sensor is electrically connected to one or more leads at least partially placed on one or both of the first and second solid element at an interface where the first and second solid element are joined.

10. The sensor according to claim 1, wherein the sensor is a Clark-type sensor.

11. The sensor according to claim 1, wherein the sensor is a microsensor.

12. The sensor according to claim 3, wherein said one or more analyte permeable openings or said chamber is further configured such that the capillary force is sufficiently low at a position that said capillary force incapable of driving said analyte permeable membrane material past said position.

13. The sensor according to claim 1, wherein for at least one of the one or more analyte permeable openings, the end of the analyte permeable membrane, which faces the chamber, is placed at:
a. the end of the at least one of the one or more analyte permeable openings, which faces the chamber,
b. a position where at least one boundary surface of at the least one of the one or more analyte permable openings presents a kink, or
c. a position z, wherein a property of the sensor defined by the expression:

$(1/A)*dA/dz$ is equal to or larger than 1/micrometer, wherein A is area of a cross-section of the at least one of the one or more of analyte permeable openings, said cross-section being orthogonal to a path through the at least one of the one or more analyte permeable openenings, and z is a position along the path through the at least one of the one or more analyte permeable openings.

14. The sensor according to claim 1, wherein one or more or all boundary walls of the one or more analyte permeable openings have a non-rectilinear shape.

15. The sensor according to claim 1, wherein the sensor endures a differential pressure of 4 bar or more.

16. The sensor according to claim 1, wherein an angle between a boundary wall of the one or more analyte permeable openings at the end of the one or more analyte permeable openings, which faces the chamber, and an abutting wall of the chamber is more than 270 degrees.

17. The sensor according to claim 1, wherein an angle between a boundary wall of the one or more analyte permeable openings at the end of the one or more analyte permeable openings, which faces the chamber, and an abutting wall of the chamber is more than 285 degrees.

18. The sensor according to claim 1, wherein the chamber comprises:
a reaction region, and
a reservoir region being connected with the reaction region, and, wherein the sensor further comprises:
a guard electrode configured to enable reduction or oxidation of at least one reactant from at least a part of the reservoir region, wherein the guard electrode comprises a thin film.

19. The sensor according to claim 1, wherein the one or more analyte permeable openings are placed at least partially between the first solid element and the second solid element.

20. The sensor according to claim 1, wherein the sensor comprises a plurality of analyte permeable openings.

21. The sensor according to claim 1, wherein one or both of:
the working electrode, and
the reference electrode,
comprise a thin film.

22. The sensor according to claim 1,
wherein a distance between:
the working electrode
and
a point in a reaction region of the chamber, which is furthest away with respect to the working electrode is 500 micrometer or less.

23. The sensor according to claim 1, wherein a distance between:
a. the working electrode
and
b. a point in a reaction region of the chamber, which is furthest away with respect to the working electrode is 50 micrometer or less.

24. The sensor according to claim 1, wherein the working electrode is a two-dimensional electrode covering an area equal to or less than 2500 square micrometer.

25. The sensor according to claim 1, wherein the shortest distance from:
a. any point on the working electrode,
through the one or more analyte permeable openings and the analyte permeable membrane to
b. a point on an opposite side of the analyte permeable membrane with respect to the working electrode,
is equal to or less than 300 micrometer.

26. The sensor according to claim 1, wherein a smallest total cross-sectional area of the one or more analyte permeable openings in a cross-sectional plane is orthogonal to a direction of movement of an analyte diffusing from the associated volume to the working electrode along the shortest possible path is equal to or less than 0.25 square millimeter.

27. The sensor according to claim 1, wherein a ratio $(A_{min,opening}/A_{min, WE-Ref})$ between
a. A first smallest total cross-sectional area $(A_{min,opening})$ of the one or more analyte permeable openings in a cross-sectional plane is orthogonal to a direction of movement of an analyte diffusing from the associated volume to the working electrode along the shortest possible path, and
b. A second smallest total cross-sectional area $(A_{min, WE-Ref})$ of the chamber along a shortest possible path of a species diffusing from the working electrode (WE) to the reference electrode (Ref), said second smallest cross-sectional area $(A_{min, WE-Ref})$ being in a cross-sectional plane is orthogonal to a direction of movement of a species diffusing from the working electrode (WE) to the reference electrode (Ref) along the shortest possible path, is equal to or less than 1.

28. The sensor according to claim 1, wherein the first solid element comprises silicon or wherein the second solid element comprises borosilicate.

29. The sensor according to claim 1, wherein the first solid element and the second solid element are bonded together.

30. The sensor according to claim 1, wherein the analyte permeable membrane comprises a polymer.

31. A method for producing a sensor according to claim 1, comprising forming the analyte permeable membrane in said one or more analyte permeable openings by at least:
   a. Adding a membrane material in a fluid form to the one or more analyte permeable openings,
   b. Removing a portion of membrane material by
      i. sawing it off,
      ii. wiping it off,
      iii. grinding it off, or
      iv. laser cutting.

32. The method according to claim 31, wherein the method further comprises solidifying the membrane material.

33. A method for sensing an analyte in an associated volume comprising contacting the sensor of claim 1 with an analyte provided in a volume of liquid or gas and sensing said analyte.

34. The method according to claim 33, wherein the analyte is hydrogen sulfide.

35. The method of claim 33, wherein the analyte is provided in a volume of sewer or waste water.

36. The method of claim 33, wherein the analyte is provided in a volume of natural gas or biogas.

37. The method of claim 36, wherein the volume of natural gas or biogas is produced in a desulfurization process.

* * * * *